US012639538B2

(12) United States Patent
Nakamura et al.

(10) Patent No.: US 12,639,538 B2
(45) Date of Patent: May 26, 2026

(54) OPTICAL INFORMATION READER

(71) Applicant: DENSO WAVE INCORPORATED, Chita-gun (JP)

(72) Inventors: Eishun Nakamura, Chita-gun (JP); Nobuyuki Fujiwara, Chita-gun (JP); Makoto Ito, Chita-gun (JP); Natsuki Mizuno, Chita-gun (JP)

(73) Assignee: DENSO WAVE INCORPORATED, Aichi-pref. (JP)

( * ) Notice: Subject to any disclaimer, the term of this patent is extended or adjusted under 35 U.S.C. 154(b) by 362 days.

(21) Appl. No.: 18/038,619

(22) PCT Filed: Nov. 22, 2021

(86) PCT No.: PCT/JP2021/042819
§ 371 (c)(1),
(2) Date: May 24, 2023

(87) PCT Pub. No.: WO2022/113938
PCT Pub. Date: Jun. 2, 2022

(65) Prior Publication Data
US 2024/0011839 A1      Jan. 11, 2024

(30) Foreign Application Priority Data

| Nov. 24, 2020 | (JP) | ................................. | 2020-194043 |
| Mar. 16, 2021 | (JP) | ................................. | 2021-042773 |
| Nov. 10, 2021 | (JP) | ................................. | 2021-183023 |

(51) Int. Cl.
*G01J 5/05* (2022.01)
*A61L 2/18* (2006.01)
(Continued)

(52) U.S. Cl.
CPC ............ *G06K 7/10712* (2013.01); *A61L 2/18* (2013.01); *G01J 5/0265* (2013.01); *G01J 5/05* (2022.01); *A61L 2202/24* (2013.01)

(58) Field of Classification Search
None
See application file for complete search history.

(56) References Cited

U.S. PATENT DOCUMENTS

| 5,576,531 A | 11/1996 | Murphy |
| 5,828,052 A | 10/1998 | Reynolds et al. |

(Continued)

FOREIGN PATENT DOCUMENTS

| JP | H06-251180 A | 9/1994 |
| JP | H07-311812 A | 11/1995 |

(Continued)

OTHER PUBLICATIONS

"Press Release—Sales of Non-contact Thermometer Started Sales Promotion Tool, Print Mall for Online Printing", Will Corporation, Inc.; 2020; https://prtimes.jp/main/html/rd/p/000000018.000058318. html [retrieved online Jan. 2022].

*Primary Examiner* — Erica S Lin
(74) *Attorney, Agent, or Firm* — Oliff PLC

(57) ABSTRACT

A configuration that enables easy implementation of wiping disinfection for a gripping handle for which an operating means is provided. The gripping handle, which is grasped by an operator, is formed as part of the lower case including part of the housing. The gripping handle is provided with an operating surface portion that the operator touches when initiating the reading process. There is a site on the inner side of the gripping handle, wherein the site is opposed to the operating surface portion. At this site on the inner surface side, a detector is provided to detect the state in which the operating surface portion is touched.

18 Claims, 24 Drawing Sheets

(51) Int. Cl.
   G01J 5/02          (2022.01)
   G06K 7/10          (2006.01)

(56)                    References Cited

U.S. PATENT DOCUMENTS

| | | | |
|---|---|---|---|
| 8,186,597 B1 | 5/2012 | Fletcher | |
| 10,025,966 B1 * | 7/2018 | Volta .................... | H02J 7/0044 |
| 2002/0049464 A1 | 4/2002 | Donofrio et al. | |
| 2002/0148902 A1 | 10/2002 | Schlieffers | |
| 2007/0165297 A1 * | 7/2007 | Sandner ............. | G02B 26/0866 |
| | | | 359/291 |
| 2012/0319847 A1 * | 12/2012 | Heller ................... | G01K 13/20 |
| | | | 600/549 |
| 2015/0146905 A1 | 5/2015 | Abe et al. | |
| 2016/0005007 A1 * | 1/2016 | Marsico ................ | G06Q 10/20 |
| | | | 705/305 |
| 2017/0108895 A1 * | 4/2017 | Chamberlin .......... | H02J 7/0044 |
| 2019/0130150 A1 | 5/2019 | Handshaw et al. | |
| 2019/0213363 A1 * | 7/2019 | Sugiura ................. | G06K 7/109 |
| 2020/0327376 A1 | 10/2020 | Stefanini et al. | |

FOREIGN PATENT DOCUMENTS

| | | | |
|---|---|---|---|
| JP | 2002-233534 A | 8/2002 | |
| JP | 2013-25518 A | 2/2013 | |
| JP | 2019-219703 A | 12/2019 | |

* cited by examiner

Figure 5:
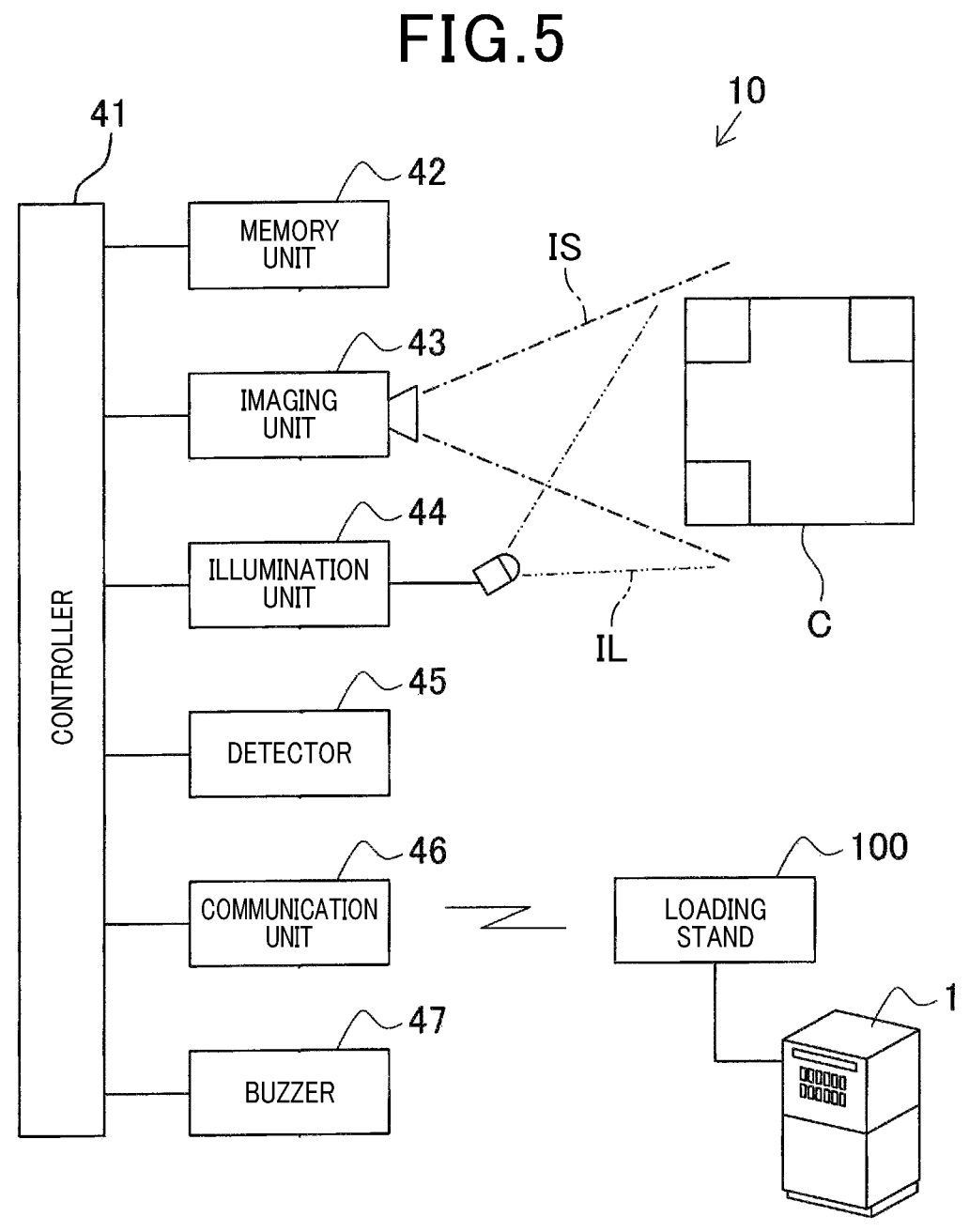

MEMORY
UNIT

10

IS

43

IMAGING
UNIT

44

ILLUMINATION
UNIT

IL

C

45

DETECTOR

CONTROLLER

46

COMMUNICATION
UNIT

100

LOADING
STAND

1

47

BUZZER

FIG.16

OPTICAL INFORMATION READER

CROSS-REFERENCE TO RELATED APPLICATION

This application is based on and claims the benefit of priority from earlier Japanese Patent Applications No. 2020-194043 filed on Nov. 24, 2020; No. 2021-042773 filed on Mar. 16, 2021; and No. 2021-183023 filed on Nov. 10, 20221 the descriptions of which are incorporated herein by reference.

TECHNICAL FIELD

The present disclosure relates to an optical information reader which is able to optically read optical information such as information codes.

BACKGROUND ART

In recent years, concern over viral infections has increased, and the spread of infections, especially within healthcare facilities, has become a major problem. Barcode readers and other optical information readers used in the medical field may also serve as a medium for bacterial and viral infections. Therefore, at least the gripping parts of the readers used at medical sites, etc., which are gripped by users, must be wiped and disinfected to prevent infection and maintain cleanliness.

CITATION LIST

Patent Literature

[PTL 1] JP-A 06-251180
It is known that an optical information reader is provided with a trigger switch etc., which is pressed and operated when starting the reading process. Such readers are configured so that the trigger switch and other switches are exposed outside through the housing that constitutes the outer contour. In such a device configuration, the trigger switch or other operating part is provided as the driving mechanism. This causes the problem that it takes time to wipe away bacteria and viruses from the driving parts, etc., and there is another concern that the wiping and disinfection may be inadequate. In the case of the barcode reader disclosed in Patent Document 1 listed above, there is exemplified a configuration that eliminates the drive portion by providing touch electrodes on both sides of the housing to detect the user's finger contact. However, even if the drive portion is eliminated in this way, a groove, step, etc. is formed between the outer edges of the touch electrodes exposed outside from both sides and the surrounding housing portion. Hence, this does not adequately solve the wiping and disinfection problem described above.

SUMMARY

Hence, it is desired to provide a configuration that enables easy implementation of wiping disinfection to the gripping handle where the operating means is provided.

With consideration of the foregoing conventional situations, an exemplary embodiment provides an optical information reader which comprises:
a reading device which optically reads optical information; and a housing which forms an accommodating space by a plurality of casings, the reading device being accommodated in the accommodating space;
wherein
the housing is provided with, as part thereof, a gripping handle gripped by a user when being used, and
the gripping handle is provided with a designated operating surface portion and a detector, the user touches the operating surface portion when making the reading device start a predetermined process in connection with reading the optical information, the detector being positioned on an inner side of the gripping handle which is opposed to the designated operating surface portion via a wall of the gripping handle and configured to detect a touch of the user on the designated operating surface portion.

The reference numbers in each of the above brackets indicate the correspondence with the specific means described in the embodiments described below.

In the exemplary embodiment, the gripping handle, which is grasped by the operator, is formed as part of the housing. The gripping handle has a predetermined operating surface portion that the operator touches when initiating a predetermined process related to the reading device. The gripping handle is provided with a detector that detects the state that the determined operating surface portion is being touched. The detector is provided, in the gripping handle, at a position that is on the inner side of the gripping handle relative to the predetermined operating surface portion.

This allows the detector to be utilized as a means of operation performed by the operator, and the detector is provided on the inner surface of the gripping handle. Therefore, the above predetermined operating surface portion and its surroundings can be composed of only an outer surface of the housing without grooves, steps, etc. to be formed thereon. Therefore, it is possible to realize an optical information reader on which it is possible to easily perform wiping and disinfection on the gripping handle where various operating means are provided.

In a further exemplary embodiment, the gripping handle is formed at a part thereof, the part being formed by one of the plurality of cases and excluding a joint left between the cases. Hence, any joint made between cases can be formed on the gripping handle, thereby making it easier to wipe and disinfect the gripping handle.

In another exemplary embodiment, the detector is provided as a piezoelectric sensor capable of sensing distortion caused on the predetermined operating surface portion. This allows the operator to press a given operating surface portion with a finger even when the operator is holding the gripping handle, thereby improving the workability of reading and other operations.

In another exemplary embodiment, the detector is provided as a capacitive sensor capable of sensing changes in a capacitance caused on the predetermined operating surface portion. In other words, there is no need to form gripping handles and housings so that the operating surface portion is distorted in a given state by the operator's operation, thereby reducing the variation in dimensional accuracy required for gripping handles and housings.

In another exemplary embodiment, the cases have a part composing and providing the predetermined operating surface portion, the part composing and providing the predetermined operating surface portion being made thinner than a remaining part of the cases. This makes it easier for the detector to detect the state in which the operating surface portion is being touched, thereby increasing the detection accuracy by the detector, i.e., the operability of the device.

In another exemplary embodiment, the optical information reader comprises a vibrator which vibrates when the state where the predetermined operating surface portion is touched by the operator is detected, the vibrator being arranged at another position in the operating handle, which is opposed to the predetermined operating surface portion. This allows the vibrator to vibrate in a predetermined state when the operator touches the operating surface portion when initiating the predetermined process, and the operator can obtain tactile feedback in response to the vibration.

In another exemplary embodiment, the optical information reader is provided with a loading stand, wherein the loading stand has a loading surface on which the optical information reader is loaded; and a magnet which is arranged at a position located inside the housing, the position being opposed to a further part of the housing. This means that, when the optical information reader is loaded on the loading stand, the magnet on the loading surface attracts the magnet on the inner side of the housing and holds the reader in place. Since the optical information reader does not need to be fixed to the loading stand, the part of the reader placed on the loading stand can be easily disinfected by wiping.

In another exemplary embodiment, since the part of the housing which is opposed to the loading surface is not the gripping handle, the gripping handle does not come in contact with the loading stand during its loading, and thus the gripping handle can be kept cleaner.

In another exemplary embodiment, the predetermined operating surface portion is formed to have a central surface portion and a peripheral surface portion around the central surface portion, the central surface portion being protruded outward than the peripheral surface portion does, and the detector is configured to detect distortion caused in the peripheral surface portion. This makes it easier for the fingers to contact the central surface portion with the predetermined operating surface portion during operation, compared to the case where the predetermined operating surface portion is formed in a flat shape. Even if the central surface portion protrudes outward, the detector can detect the distortion that occurs in the peripheral surface portion, so that detection accuracy is not reduced.

In another exemplary embodiment, the housing is provided with a protrusion protruding inwardly and being positioned on and inside the central surface portion of the predetermined operation surface, and the detector is configured to detect distortion caused in the predetermined operating surface portion depending on amounts of inward changes of the protrusion. When the operating surface portion is touched, the central surface portion is the most deformed, whereby the amount of inward movement of the protrusion located on the inner surface side of this central surface portion can be increased. The detection accuracy of the detector, i.e., the operability of the device, can thus be improved.

In another exemplary embodiment, the reading device is configured to optically read the optical information via a reading port formed on the housing, the housing is provided with an extension which extends toward the reading port from a space between a lower edge of the reading port, the lower edge locating to face the gripping handle, and the gripping handle, and the housing houses components therein such that the optical information has a center of gravity, when the reader is projected to a predetermined surface on which the reader is loaded with both an upper edge of the reading port and a tip edge of the extension being directed downward, such that the center of gravity is contained in a range formed between a contact portion provided between the upper edge and the predetermined surface, and between a contact portion provided between the tip edge and the predetermined surface. This means that the upper edge of the reading port and the tip edge of the extension will be lower in relation to the desk surface, etc., depending on the extension's extension length. In such a state, when the optical information reader is loaded, the gripping handle can be kept cleaner because the gripping handle does not come into contact with the desk surface or other surfaces in this loaded state.

In another exemplary embodiment, the casing is provided with a sound generating unit that generates a predetermined sound, the housing has a sound emission hole for sound emission of the predetermined sound to the outside, and a double-sided tape for bonding a sheet for closing the sound emission hole to the housing has an opening larger than the sound emission hole. This also prevents the double-sided tape from covering the sound emission hole, even when double-sided tape is used to adhere the sheet to the housing to close the sound emission hole in an attempt to keep it clean. Therefore, compared to the case where even the double-sided tape covers the sound emission hole, the reduction in the sound pressure of a given sound emitted to the outside can be suppressed.

In another exemplary embodiment, the optical information reader comprises a reporting unit that reports cleaning instruction information that prompts cleaning work of the optical information reader at predetermined timing. This not only makes it easier for cleaning work to be performed at the right time for that cleaning work, but also prevents forgetting to perform the work.

In another exemplary embodiment, the reporting unit receives instructions from an upper-level terminal and reports the cleaning instruction information. This allows the upper-level terminal to easily adjust the timing of reporting cleaning instruction information.

In another exemplary embodiment, the optical information reader comprises an acquiring unit for acquiring worker information that identifies a worker who has performed the cleaning work, and a memory unit in which the worker information acquired by the acquiring unit is stored together with information on the cleaning work. This allows not only easy management of work history, etc. based on the information stored in the memory unit, but also easy adjustment of the timing of reporting the above cleaning instruction information according to the actual work situation.

In another exemplary embodiment, the optical information reader comprises a cleaning work detector capable of detecting a state in which cleaning work has been performed on the optical information reader, and the memory unit stores, therein, detection results detected by the cleaning work detector. This allows a more reliable work history to be kept, and the timing of reporting the above cleaning instruction information can be adjusted to the actual situation.

In another exemplary embodiment, at least part of the information stored in the memory unit is transmitted to an upper-level terminal, and the reporting unit receives instructions from the upper-level terminal and reports the cleaning instruction information. This allows the upper-level terminal to easily collect the work history regarding the controlled optical information reader, so that the timing of reporting the above cleaning instruction information can be appropriately adjusted to the actual work situation.

In another exemplary embodiment, the optical information reader comprises: a body temperature measuring device capable of measuring a body temperature of a patient when patient information identifying the patient is read from the optical information by the reading device, and a determination unit for determining whether the patient is in a febrile state based on the results of the measurement by the body temperature measuring device. This makes it possible to not only measure a patient's body temperature with an optical information reader that can be easily wiped clean and disinfected, but also to easily determine whether the patient has a fever, thereby reducing the nursing burden on the patient.

In another exemplary embodiment, the reading device optically reads the optical information through a reading port formed in the housing, the housing is provided with an extension extending in a laminate shape in a direction toward the reading port from between the gripping handle side edge of the reading port and the gripping handle, and a coil for wireless power transmission is disposed within the extension. Thus, because the coil for wireless power transmission is placed in the extension extending in a thin plate shape, the heat generated in the coil during power transmission is dissipated from both surfaces of the extension, which are opposed to the reading port and the gripping handle, respectively. The longer the extension length, the larger the heat dissipation area by the surfaces opposed to the reading port and the gripping handle. Thus it is possible to improve the heat dissipation related to the heat generated by the coils for wireless power transmission in accordance with the extension length.

In another exemplary embodiment, the coil for wireless power transmission is bonded to an inner surface of the housing portion comprising the extension, the inner side to which the coil is bonded being located closer to the reading port than a remaining of the inner side thereof is. When the surface of the extension which is opposed to the gripping handle (hereinafter referred to as the "loading-side surface") is placed on the charging surface of the charger to receive power supply, the loading-side surface has poor heat dissipation due to the proximity of the charging surface. Meanwhile, the surface of the extension which is opposed to the reading port (hereinafter referred to as the reading port side surface) is hardly affected by the charging surface in terms of its heat dissipation. For this purpose, the coil for wireless power transmission is bonded to a part of the inner surface of the housing portion composing the extension, in which the part is opposed to the reading port. Hence, heat generated in the coil for wireless power transmission during charging is more easily transferred to the reading port side surface, which has better heat dissipation, so that the heat dissipation effect by the thin-plate extension can be further improved.

BRIEF DESCRIPTION OF DRAWINGS

In the accompanying drawings:

FIG. 5 is a block diagram exemplifying an outline of electric configurations and some other configurations of the optical information reader;

FIG. 16 is a perspective view showing a feature of an optical information reader according to a seventh embodiment;

DESCRIPTION OF THE EMBODIMENTS

First Embodiment

Figure 1:
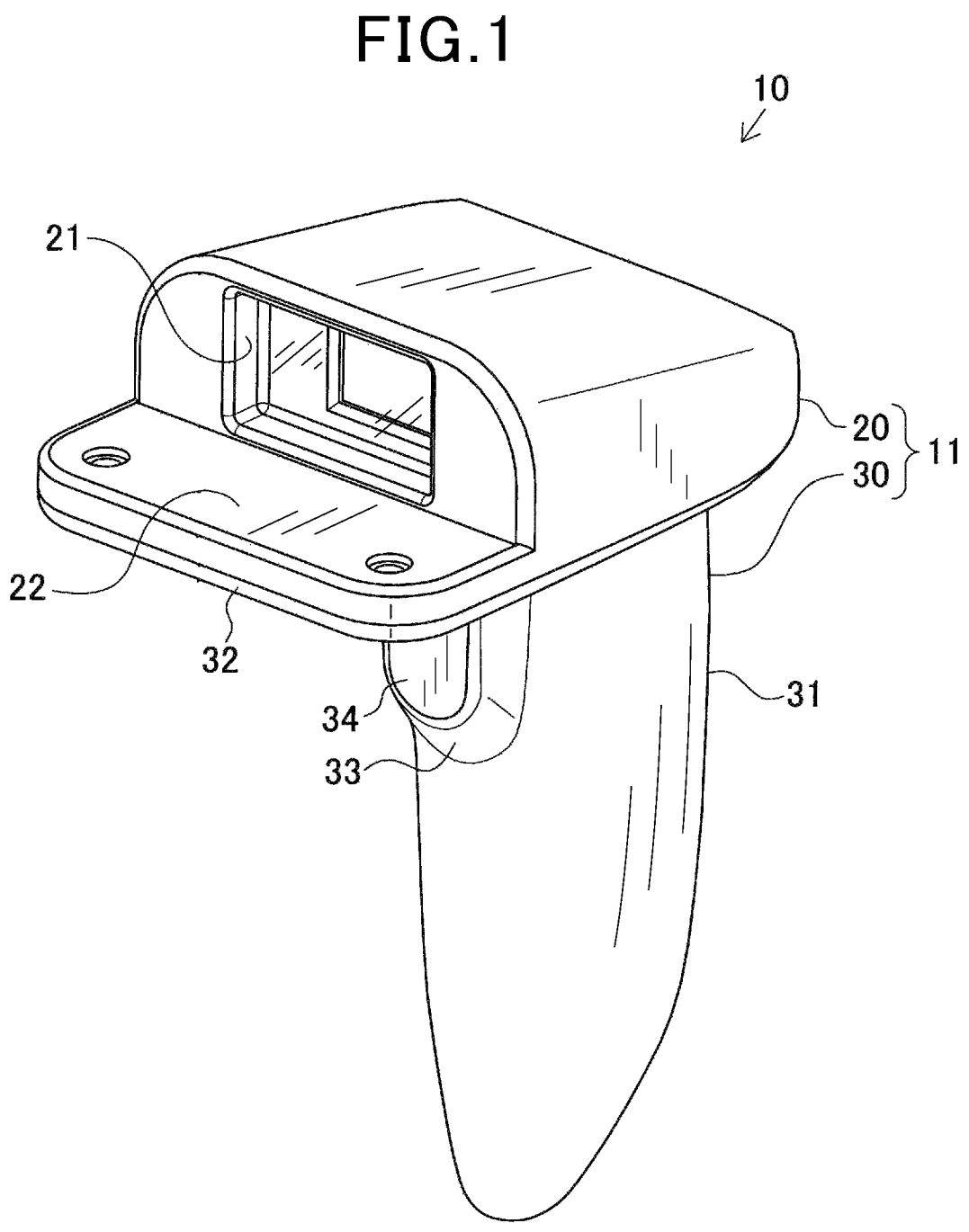
FIG. 1 is a perspective view showing an optical information reader according to a first embodiment.
Figure 2:
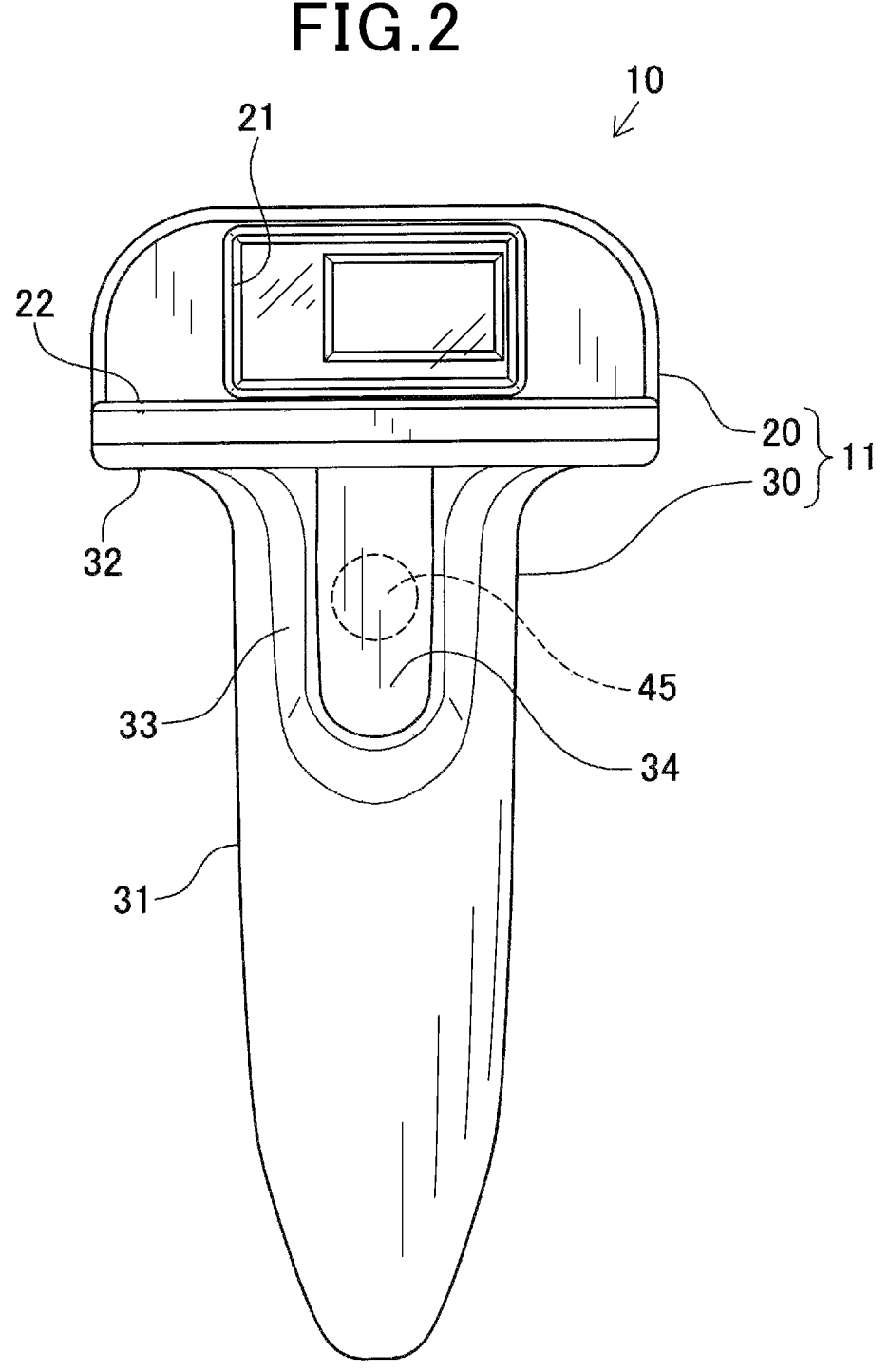
FIG. 2 is a frontal view of the optical information reader shown in FIG. 1.
Figure 3:
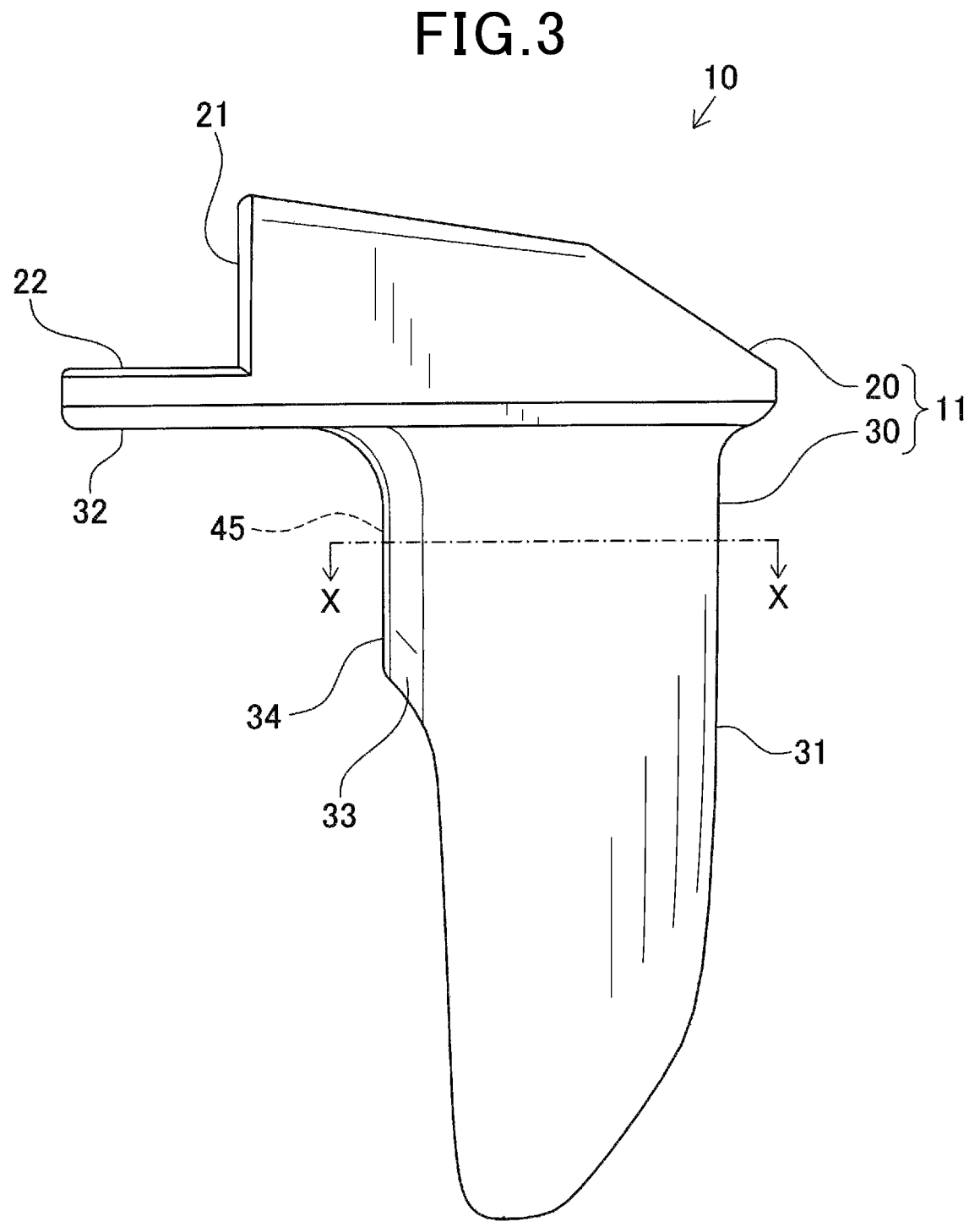
FIG. 3 is a side view of the optical information reader shown in FIG. 1.
Figure 4:
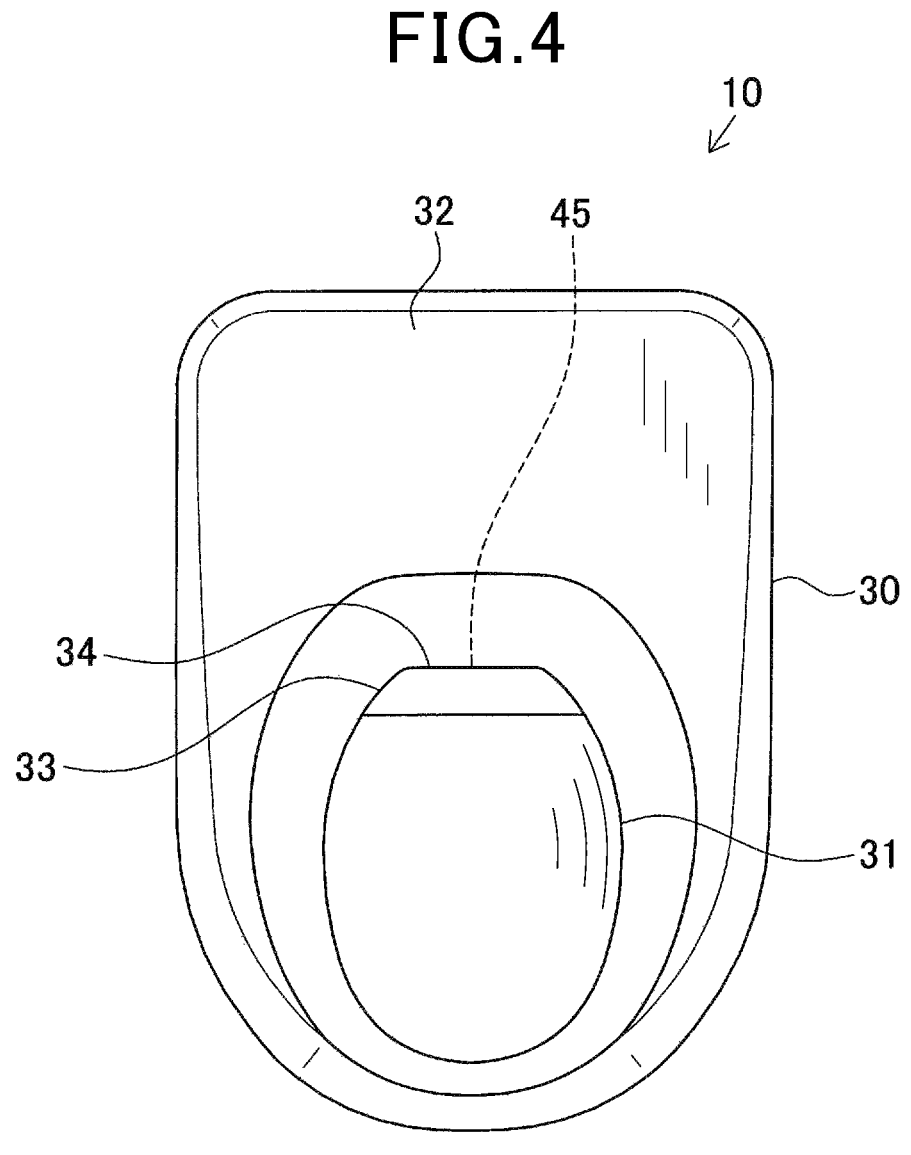
FIG. 4 is a bottom view of the optical information reader shown in FIG. 1.

With reference to the accompanying drawings, a first embodiment of an optical information reader according to the present invention will now be described.

The present embodiment provides an optical information reader configured as a portable reading device which is able to optically read information, i.e., optical information, such as information codes (for example, a barcode and a QR code (registered trademark).

As shown in FIGS. 1 to 4, the optical information reader 10 has a housing 11 that constitutes its outer contour. The housing 11 has an upper case 20 through which a reading port 21 is formed and a lower case 30 to which a gripping handle 31 is formed, which is grasped or gripped by an operator. The upper case 20 and the lower case 30 are mutually assembled to form a housing space for various electronic components. The upper case 20 is formed to provide the reading port 21. The upper case 20 is provided with a guide 22 extending in the direction in which the reading port 21 is directed (hereinafter, the direction is also referred to as forward direction or frontward direction) to facilitate the orientation of the reading port 21 toward the information code. The guide 22 has a top surface which is parallel to the combined surfaces of the upper case 20 and lower case 30.

The lower case 30 is formed to mutually integrate the assembly part 32, which is assembled below the upper case 20, such as the guide 22, and the gripping handle 31, which constitutes a lower part of the lower case 30 which is lower than the assembly part 32 in the up and down directions. The gripping handle 31 is formed so that there are no grooves on its outer surface to facilitate wiping and disinfection, and has a connection part connected with an assembly part 32 is also formed to be smoothly curved.

The gripping handle 31 is provided with an operating base 33 that smoothly protrudes forward at a position below the guide 22, where the operating base 33 can be touched by fingers holding the gripping handle 31. The operating base 33 is configured so that a flat surface located in front functions as an operating surface portion 34 that is distorted by being pressed when the reading process to read the information code is started (hereinafter referred to as "reading start operation"). Specifically, the operating base 33 is formed so that the thickness (wall thickness) t of the lower case 30 of the portion providing the operating surface portion 34 is thinner than the thickness of the lower case 30 providing the other portions thereof in order to facilitate distortion of the operating surface portion 34. For example, if the thickness of the lower case 30 comprising the other portions is formed to be about 1.5 to 2 mm, the thickness t of the lower case 30 at the portion providing the operating surface portion 34 is formed to be about 0.7 to 1.5 mm.

Next, the electrical configuration of the optical information reader 10 is described with reference to the drawings. As shown in FIG. 5, the optical information reader 10 is provided with a controller 41 comprising a CPU or the like, a memory unit 42 comprising ROM, RAM, nonvolatile memory, or the like, and an imaging unit 43 configured as an optical camera provided with a light-receiving sensor (for example, a C-MOS area sensor, CCD area sensor, etc.). In addition, this optical information reader 10 is equipped with an illumination unit 44 that irradiates illumination light toward the imaging field of view of the imaging unit 43 and a detector 45 that detects the reading start operation performed for the operating surface portion 34. In addition, this optical information reader 10 is equipped with a communication unit 46 that is configured as a communication interface for wireless communication with external devices such as a loading stand 100 such as a cradle and an upper-level terminal 1 such as a management server, and a buzzer 47 that can emit buzzer sounds such as beeps and alarm sounds. At least some of these various electronic components are housed in the housing space provided by the upper case 20 and the lower case 30 of the housing 11. For example, the imaging unit 43 and illumination unit 44 are housed in the upper case 20 so that the imaging unit 43 has an imaging range in front through the reading port 21 and the illumination unit 44 illuminates the imaging field of view through the reading port 21.

Figure 6:
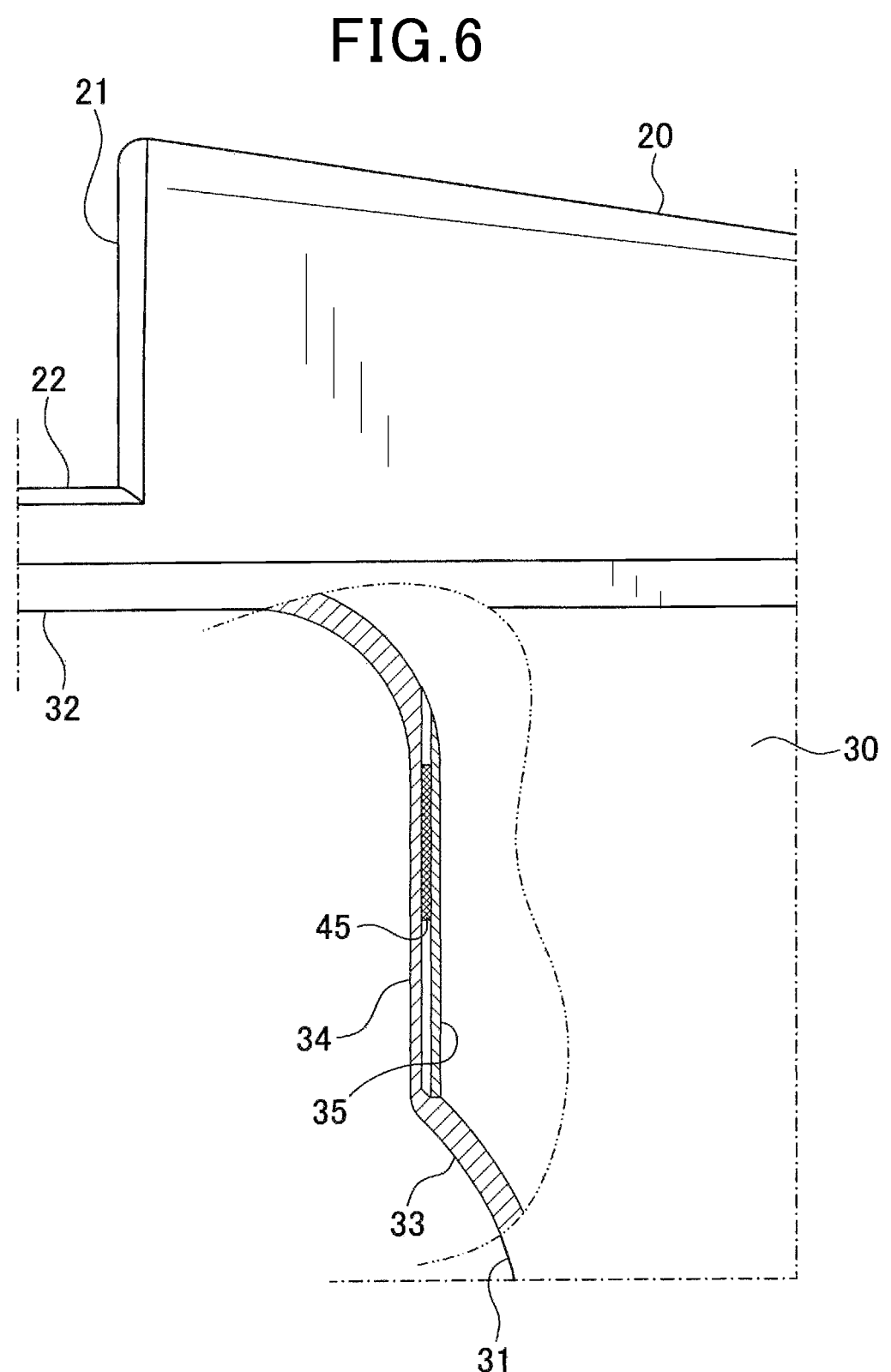
FIG. 6 is a partially enlarged sectional view explaining how a detector is arranged, as its configuration, in the optical information reader.

The detector 45 is a piezoelectric sensor (piezoelectric element sensor) for detecting strain generated in the operating surface portion 34. As shown in FIG. 6, the detector 45 is supported (held) by a support plate 35 at a location (i.e., an area or site) on the inner side of the gripping handle 31 via the wall of the gripping handle so as to be opposed to the operating surface portion 34 formed in the front of the wall. The detector 45 is configured to output a predetermined operation detection signal to the controller 41 when the distortion of the operating surface portion 34 exceeds a predetermined value, as an operation to start reading has been performed.

Figure 7:
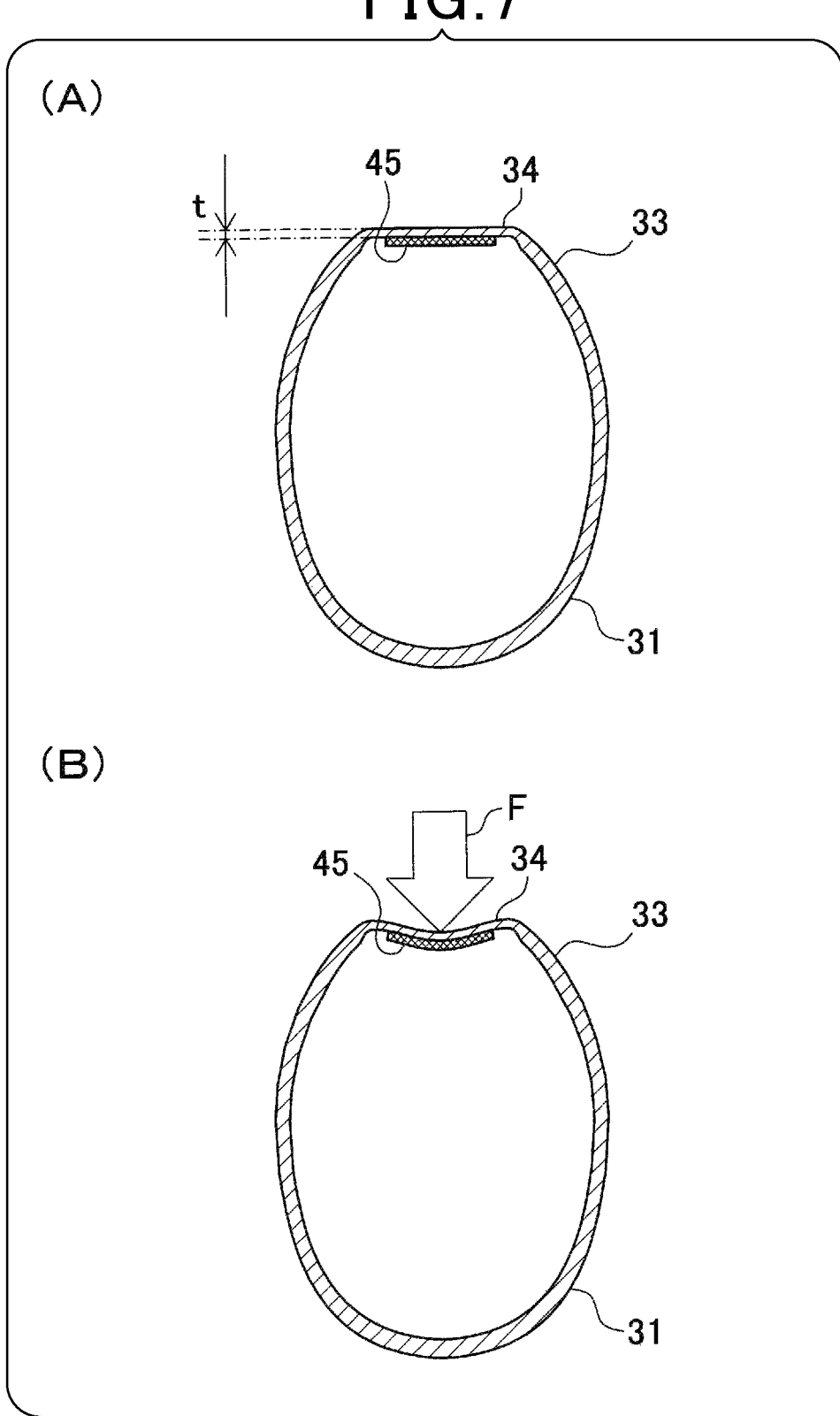
FIG. 7, part (A) thereof, is an explanatory diagram along a section taken along a X-X line in FIG. 3, explaining when an operating surface portion of the optical information reader has not been subjected to a reading start operation, and FIG. 7, part (B) thereof, is an explanatory diagram along the section taken along the X-X line in FIG. 3, explaining when the operating surface portion of the optical information reader has been subjected to the reading start operation.

Specifically, for example, as shown in part (A) of FIG. 7, if the distortion detected by the detector 45 is less than the predetermined value because the operating surface portion 34 is not distorted, the operation detection signal is not outputted to the controller 41 as no reading start operation is performed on the operating surface portion 34. On the other hand, as shown in part (B) of FIG. 7, when the distortion detected by the detector 45 exceeds the above predetermined value because the operating surface portion 34 is distorted by a predetermined amount or more of pressure, the operation detection signal is outputted to the controller 41 as a reading start operation (see an arrow F in part (B) of FIG. 7 is performed on the operating surface portion 34. In parts (A) and (B) of FIG. 7, the parts housed on the inner surface side of the gripping handle 31 are omitted from being drawn for convenience, except for the detector 45.

By receiving the foregoing detection signal from the detector 45, the controller 41 is configured to start a reading process using the captured image of an information code C (see FIG. 5) captured by the imaging unit 43, and to decode the data recorded in the information code C in this reading process using a predetermined decoding method. The reading results, etc. obtained in such a reading process are wirelessly transmitted to the upper-level terminal, etc. via the communication unit 46 at predetermined timing. The controller 41, as serving together with the imaging unit 43, corresponds to an example of a "reading device" that optically reads optical information such as information code C, and is housed in the housing space provided by the housing 11.

As explained above, in this embodiment of the optical information reader 10, the gripping handle 31 that is grasped by the operator is formed as part of the lower case 30 partly composing the housing 11. The gripping handle 31 has an operating surface portion 34 to which the operator touches when initiating the reading process. The detector 45 is provided at a site (area) on the inner side of the gripping handle 31, where the site is opposed to the operating surface portion 34 via a wall of the gripping handle 31. The detector 45 is configured to detect the state in which the operating surface portion 34 is being touched by an operator.

This allows the operator to use the detector 45 as a means of operation. In particular, since the detector 45 is provided on the inner surface of the gripping handle 31, the operating surface portion 34 and its surroundings can be composed only of the outer surface of the lower case 30 without grooves or steps formed on the outer surface thereof. Therefore, it is possible to realize the optical information reader that on which it is possible to easily perform wiping and disinfection on the gripping handle 31 where the operating means are provided.

In particular, the gripping handle 31 is formed at a site on the lower case 30 where three are no joints for mutually jointing cases. This eliminates the joints between cases from the outer surface of the gripping handle 31, thus making it easier to perform wiping and disinfection on the gripping handle 31.

And the detector 45 is composed of a piezoelectric sensor capable of detecting the strain generated in the operating surface portion 34. This allows the operator to press the operating surface portion 34 with a finger(s) even while holding the gripping handle 31, thus improving the workability of reading and other operations.

The detector 45 is not limited to being configured by a piezoelectric sensor. Instead, the detector 45 may be configured by other sensing means capable of detecting that the operating surface portion 34 is being touched, for example, such as a capacitive sensor capable of detecting changes in capacitance generated in the operating surface portion 34. When the detector 45 is configured with a capacitive sensor, there is no need to form the gripping handle 31 and housing 11 so that the operating surface portion 34 is distorted to a predetermined state by the operator's operation, thereby reducing the variation in dimensional accuracy required for the gripping handle 31 and housing 11.

The thickness t of the lower case 30 of the site providing the operating surface portion 34 is formed to be thinner than the thickness of the lower case 30 providing the other remaining portions (see FIG. 7). This makes it easier for the detector 45 to detect the state in which the operating surface portion 34 is being touched, thereby increasing the detection accuracy required for the detector 45, i.e., the operability of the device.

Figure 8:
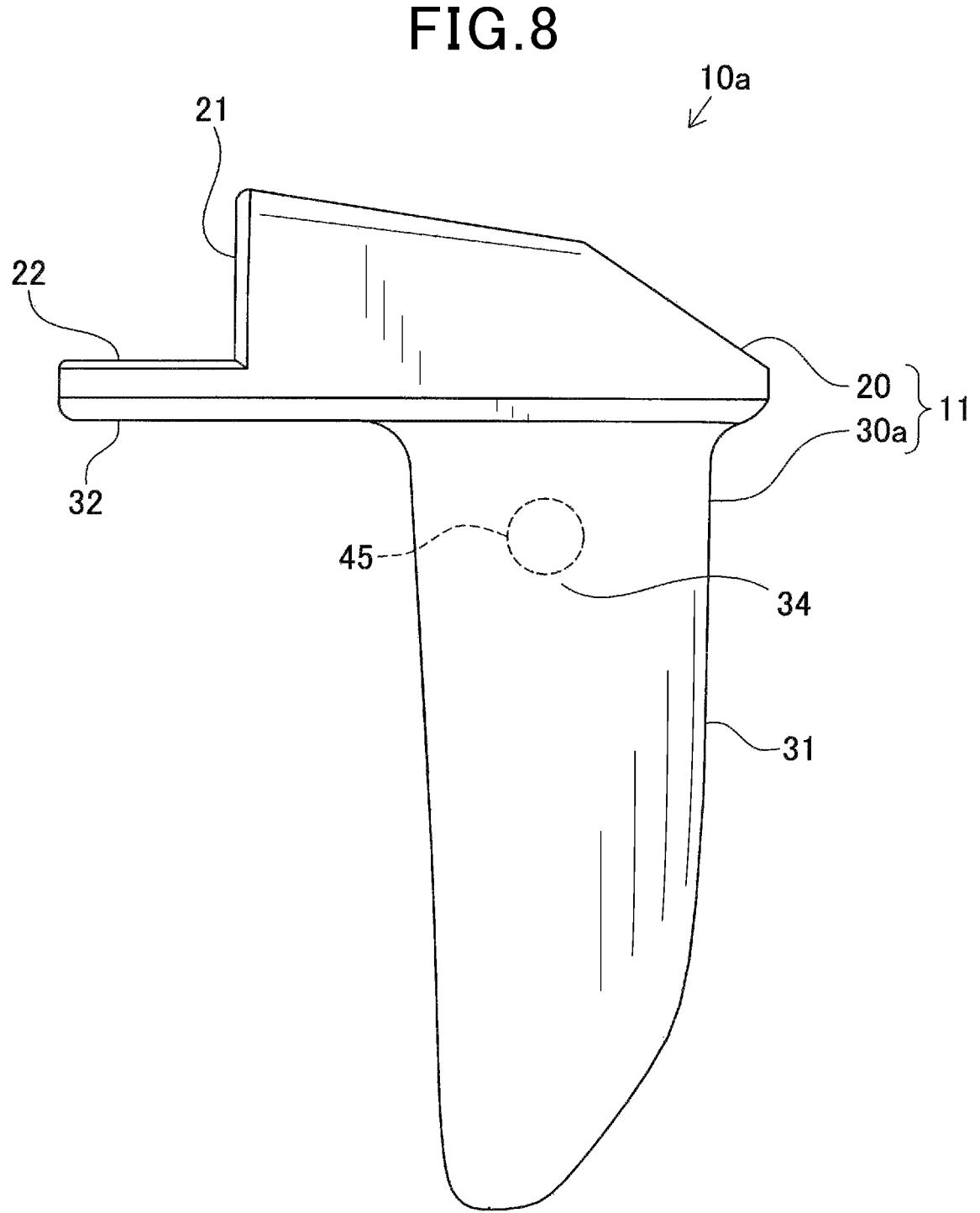
FIG. 8 is a side view of an optical information reader according to a modification of the first embodiment.

The operating surface portion 34 on which the detector 45 is provided on the inner surface side is not always limited to being configured as a flat surface located in front of the gripping handle 31. Alternatively, the operating surface portion 34 may also be configured as a curved surface located in front of the gripping handle 31, for example. The operating surface portion 34 may be provided on one side of the gripping handle 31 in the left-right direction orthogonal to the front-back direction, such as in the lower case 30a of the optical information reader 10a, as illustrated in FIG. 8. In this modification, such a one side may be configured as a curved surface or as a smooth protruding flat surface like the operating base 33.

Furthermore, the operating surface portion 34 may be provided on each of the foregoing left and right sides of the gripping handle 31. When a pair of operating surface portions 34 is provided on the left and right side of the gripping handle 31, the state where the fingers pinching the gripping handle 31 touch the respective operating surface portions 34 can be detected by the detector 45. This detection can be used as detection of the foregoing reading start operation.

Second Embodiment

Next, the optical information reader of a second embodiment of the invention will now be described with reference to the drawings.

The second embodiment differs from the first embodiment mainly in that the device provides tactile feedback to the operator during operation. Therefore, the same reference numbers are attached to the component parts that are substantially the same or similar as or to those in the first embodiment, and the redundant description is omitted.

Figure 9:
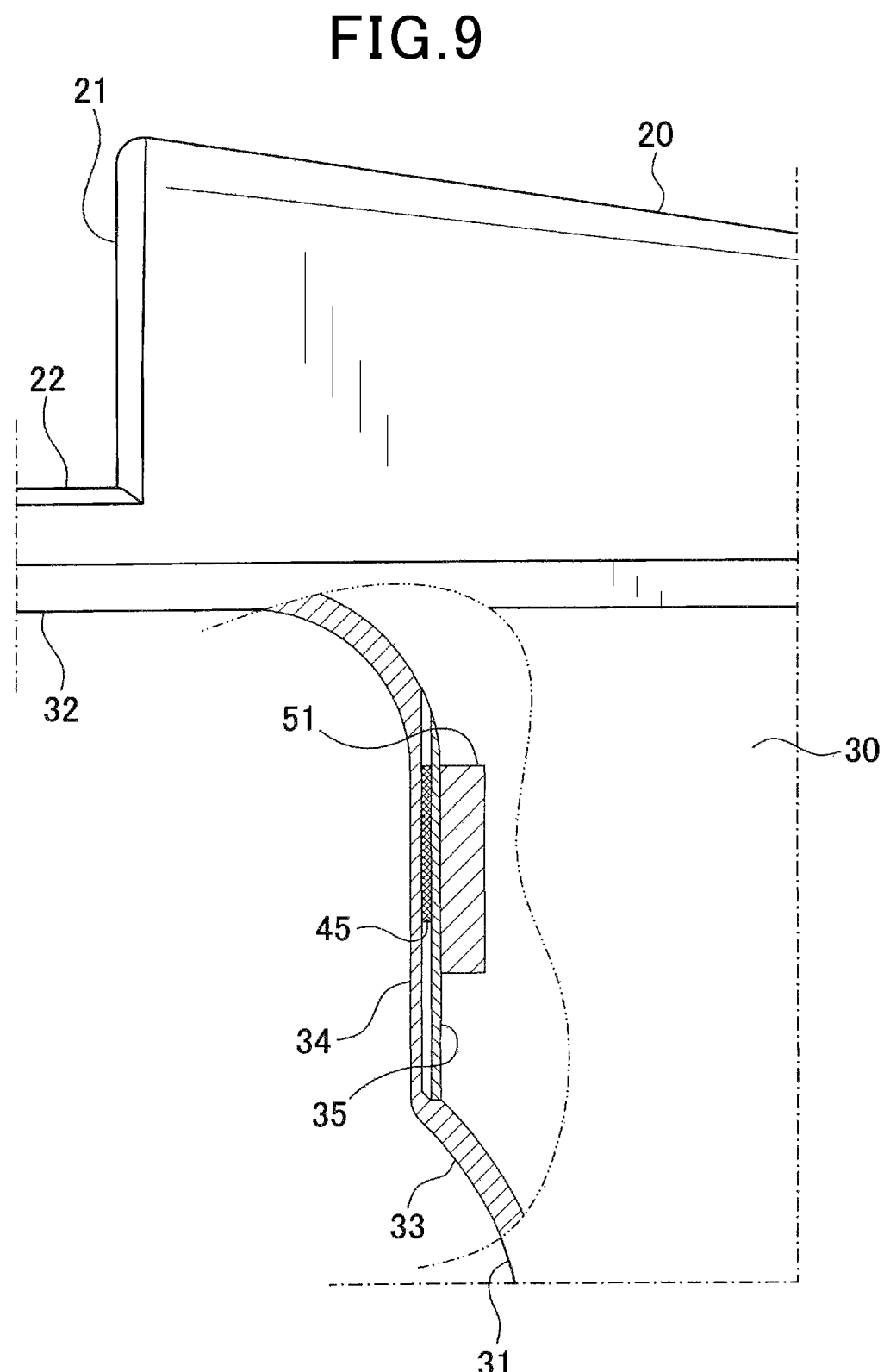
FIG. 9 is a partially enlarged sectional view showing a part according to the feature of the optical information reader of a second embodiment.

In this embodiment, the state in which the operating surface portion 34 is touched by the site (part) of the inner side surface of the gripping handle 31, which is opposed to the portion 34, is also detected by the detector 45. In this configuration, as shown in FIG. 9, a vibration actuator 51 is provided as a vibrator that vibrates at a predetermined vibration state in response to control by controller 41.

As a result, when the operator touches the operating surface portion 34 to start the above reading process, the vibration actuator 51 vibrates at a predetermined vibration state. Therefore, the operator can obtain tactile feedback in response to the vibration. The vibration actuator 51 may be configured to vibrate by an ERM method, by an LRA method, or a piezoelectric method, for instance.

The characteristic configuration of this embodiment, in which the vibration actuator 51 provides the operator with tactile of feedback, can be applied to other embodiments and their modifications.

Third Embodiment

Next, the optical information reader of the third embodiment of the invention will now be described with reference to the drawings.

The third embodiment differs from the first embodiment mainly in that the device uses magnets for fixing to the loading stand to facilitate the wiping and disinfection work. Therefore, the same reference numbers are attached to the component parts that are substantially the same or similar as or to those of the first embodiment, and their descriptions are omitted.

Generally, when a portable reading device is placed on a charger or a loading stand such as a cradle, it is desired that the device should not be easily moved from the placed state. In such a case, it is possible to provide a configuration with concave-convex shapes for engaging and securing both the reading device and the loading stand. However, the problem is that the uneven shape makes it time-consuming and difficult to perform the wiping and disinfection work.

Figure 10:
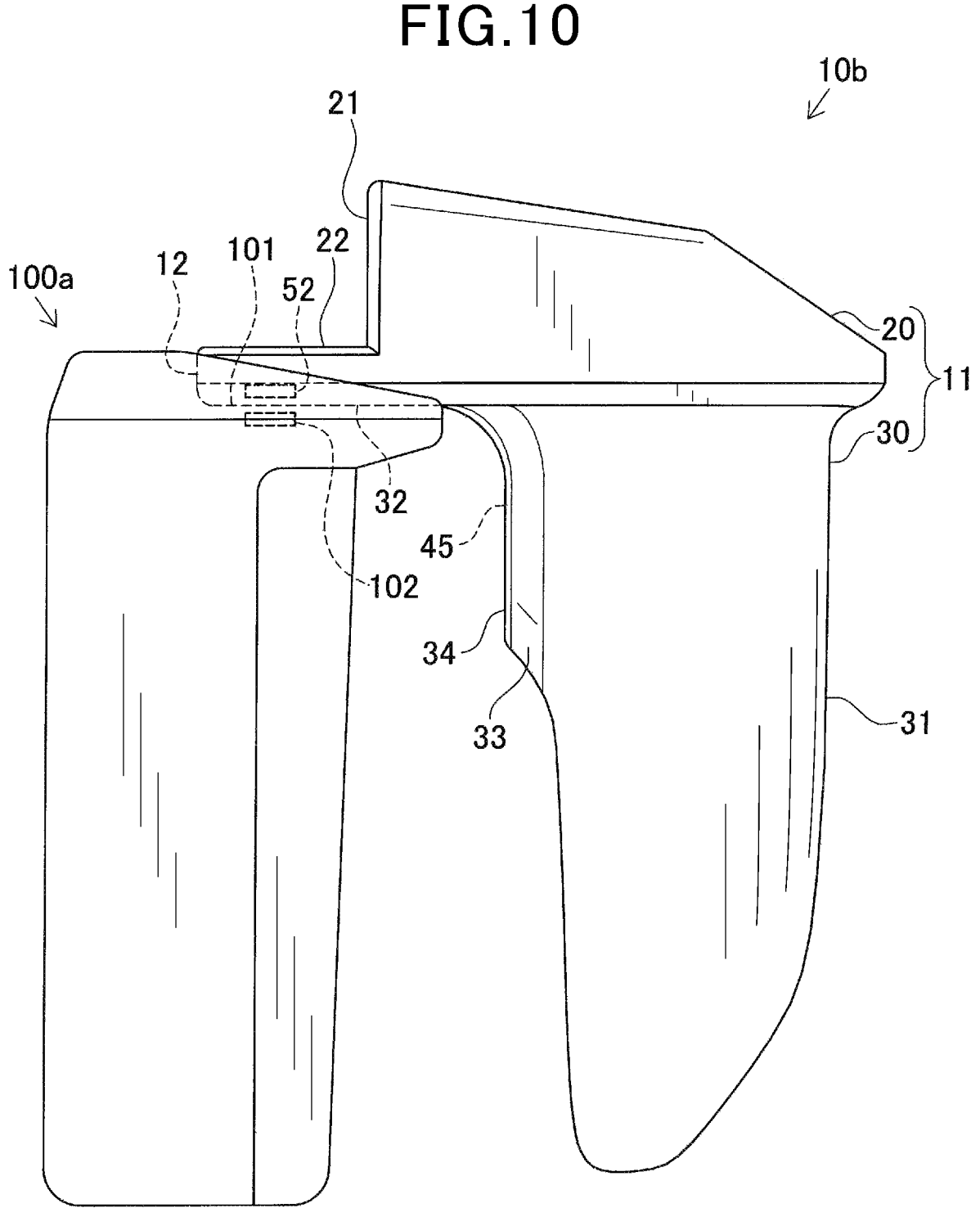
FIG. 10 is a side view showing both an optical information reader and a loading stand.

For this reason, as shown in FIG. 10, in the loading stand 100a on which the optical information reader 10b is placed, a magnet 102 is provided at a position that is the inner surface side of the loading surface 101. In the optical information reader 10b, a magnet 52 is provided at a position on the inner surface of the housing 11 that is opposed to the loading surface 101 when being loaded on the loading stand. In the present embodiment, an extension 12 is formed by the guide 22 of the upper case 20 and a part of the assembly part 32 extending forward in the lower case 30. This extension 12 is a portion that extends from between the lower edge of the reading port 21 which faces the gripping handle and the gripping handle 31 in the direction along which the reading port 21 is directed. The protrusion is formed into, almost, a thin plate. This extension 12 is positioned as a part of the housing 11 that faces the loading surface 101 when being loaded. At a predetermined position on the inner surface side of the extension 12, the magnet 52 is provided.

As a result, when the optical information reader 10*b* is loaded on the loading stand 100*a*, the magnet 102 of the loading surface 101 and the magnet 52 of the extension 12 attract each other to secure the reader and stand together. This eliminates the need for uneven surfaces and other means for engaging and securing the optical information reader 10*b* to the loading stand 100*a*. Thus, wiping and disinfection of the area to be placed on the loading stand 100*a* can be easily performed.

In particular, as can be seen in FIG. 10, a part of housing 11 that faces the loading surface 101 when being loaded is the extension 12, and not the gripping handle 31. Therefore, the gripping handle 31 does not come in contact with the loading stand 100*a* during the loading placement, and the gripping handle 31 can be kept cleaner.

The magnet 52 used for the fixedly loading is not limited to being placed on the inner surface side of the extension 12. The magnet 52 should be placed on the inner surface side of a portion of housing 11 where the portion is opposite the loading surface, when the device is loaded on the loading stand.

The characteristic configuration of this embodiment and its modification that utilize the fixing magnet 52 can be applied to the other embodiments and modifications.

Fourth Embodiment

With reference to the accompanying drawings, an optical information reader according to a fourth embodiment of the present invention will now be described.

The fourth embodiment differs from the first embodiment, described above, mainly in that the predetermined operating surface portion is formed so that the operator's fingers can easily contact the operating surface portion during operations. Therefore, the same symbols are attached to the components that are substantially the same as those in the first embodiment, and their descriptions are omitted from being redundant.

Figure 11:
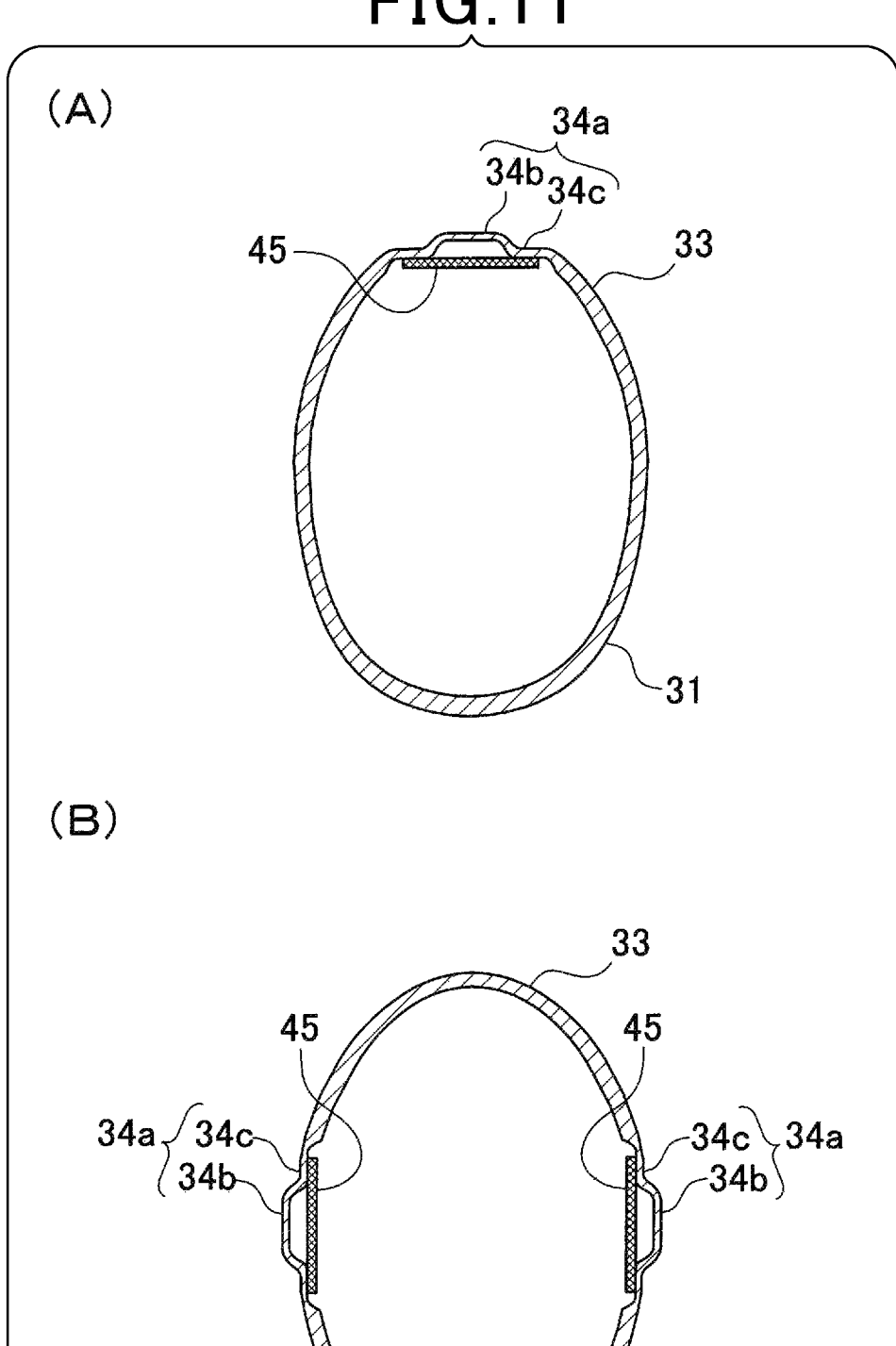
FIG. 11, part (A) thereof, is an explanatory diagram along a section taken along the X-X line in FIG. 3, outlining a feature of an optical information reader according to a fourth embodiment, and FIG. 11, part (B), is an explanatory diagram along the section taken along the X-X line in FIG. 3, outlining a feature of an optical information reader according to a modification of the fourth embodiment.

As shown in part (A) of FIG. 11, the operating surface portion 34*a* is formed so that the central portion 34*b* thereof protrudes outwardly with respect to the peripheral portion 34*c* thereof. The detector 45 is configured, for example, by a piezoelectric sensor so that the strain generated in the outer circumference 34*c* can be detected.

This makes it easier for the fingers of an operator to contact the operating surface portion 34*a* at its central surface portion 34*b* during its contact operation, compared to the case where the operating surface portion 34 is formed in a flat shape. Even if the central surface portion 34*b* protrudes outward, the detector 45 can detect the distortion that occurs in the periphery area 34*c*. Therefore, detection accuracy of the sensor is not reduced.

As a modification of the present embodiment, the operating surface portion 34*a* may be provided on each of the left and right sides of the gripping handle 31 which are orthogonal in the direction to the front-back directions, as illustrated in part (B) of FIG. 11. In such a confirmation according to the modification, the operating surface portion 34*a* may be formed on only one of the left and right sides.

The characteristic configuration of this embodiment and its modifications, in which operating surface portion 34*a* is formed so that central surface portion 34*b* protrudes outward with respect to peripheral surface portion 34*c*, can be applied to other embodiments and their modifications.

Fifth Embodiment

With reference to the accompanying drawings, an optical information reader according to a fifth embodiment of the present invention will now be described.

A fifth embodiment differs from the first embodiment, described above, mainly in that the center of gravity of the reader is adjusted so that the gripping handle 31 can be loaded on the upper side of the optical information reader. Therefore, the same symbols are attached to the components that are substantially the same as those in the first embodiment, and their descriptions are omitted.

When a portable reading device or other device is placed on a predetermined surface such as a desk surface S, a part of the gripping handle may contact the desk surface S, and thus become dirty or being contaminated.

Therefore, in this embodiment, the optical information reader 10 is configured to be placed on the desk surface S with the gripping handle 31 upward. For this purpose, a structure is adopted in which an extending portion 12 that extends in the direction toward which the reading port 21 faces from between the lower edge that is the gripping handle side of the reading port 21 and the gripping handle 31 is utilized. This utilization structure adjusts the center of gravity position G of the optical information reader 10 so that the reader can be placed on the desk surface S.

Figure 12:
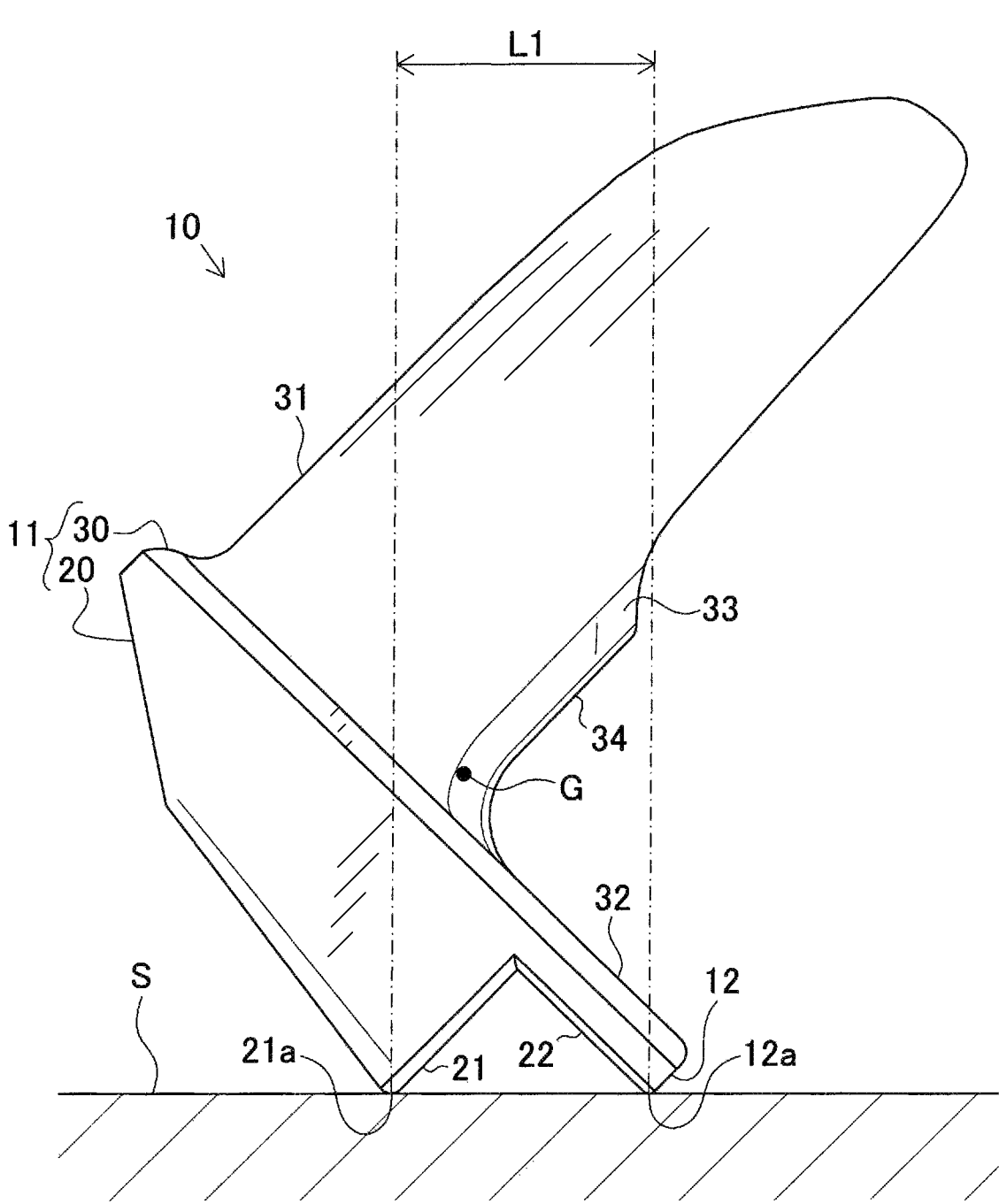
FIG. 12 is a side view showing how an optical information reader according to a fifth embodiment is loaded.
Figure 13:
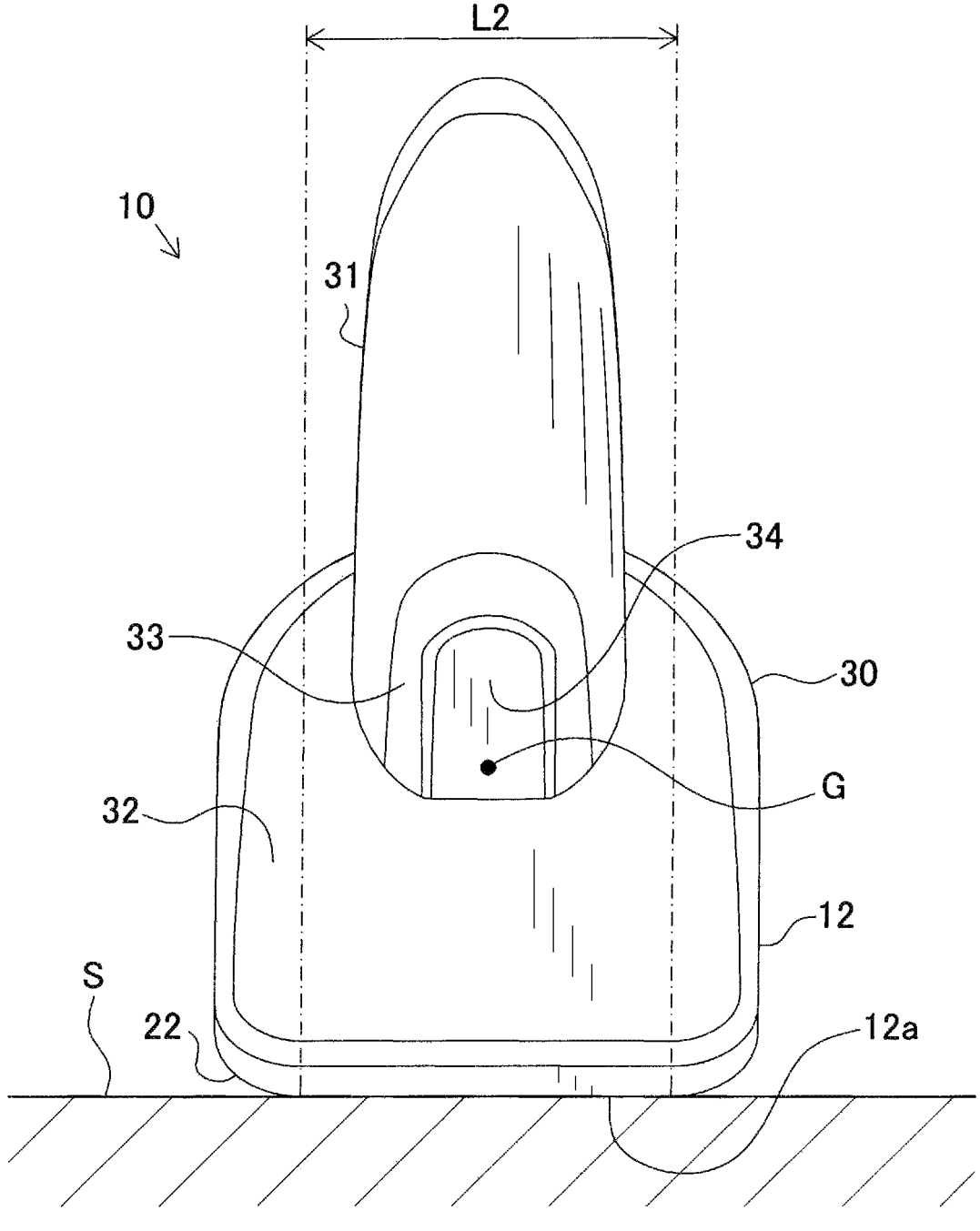
FIG. 13 is a frontal view showing how the optical information reader according to the fifth embodiment is loaded.

Specifically, as shown in FIGS. 12 and 13, in the present embodiment, the reader is placed on the desk surface S with an upper edge 21*a* of the reading port 21 and a tip edge 12*a* of the extending portion 12 being downward. In this case, the positions of various electronic components housed in housing 11 are adjusted so that the center of gravity position G of the optical information reader 10 projected on the desk surface S is included in the range (see the reference symbols L1 in FIGS. 12 and L2 in FIG. 13) bounded by both a contract portion provided between the upper edge 21*a* and the desk surface S, and a contact portion provided between the tip edge 12*a* and the desk surface S.

As a result, the optical information reader 10 can be placed on the desk surface S with the upper edge 21*a* of the reading port 21 and the leading edge 12*a* of the extending portion 12 being below. In this loaded state of the gripping handle 31, the gripping handle 31 does not come in contact with the desk surface S, so the gripping handle 31 can be kept cleaner or prevented from being contaminated.

In particular, in this embodiment, the extension length of the extending portion 12 is set so that the direction of extension of the gripping handle 31 relative to the desk surface S is about 45° in the foregoing loaded state. This not only increases postural stability in the foregoing loaded state, but also makes it easier to hold the gripping handle 31 from the foregoing loaded position.

The characteristic configuration of this embodiment, in which the center of gravity position G is adjusted so that the gripping handle 31 can be loaded so as to be faced upward, can be applied to other embodiments and their modifications.

Sixth Embodiment

With reference to the accompanying drawings, an optical information reader according to a sixth embodiment of the present invention will now be described.

The sixth embodiment differs from the first embodiment, described above, mainly in that sound emission holes are closed so as to suppress the decrease in sound pressure of the buzzer sound emitted to the outside. Therefore, the same symbols are applied to the components that are substantially the same as those in the first embodiment, and their descriptions are omitted.

Figure 14:
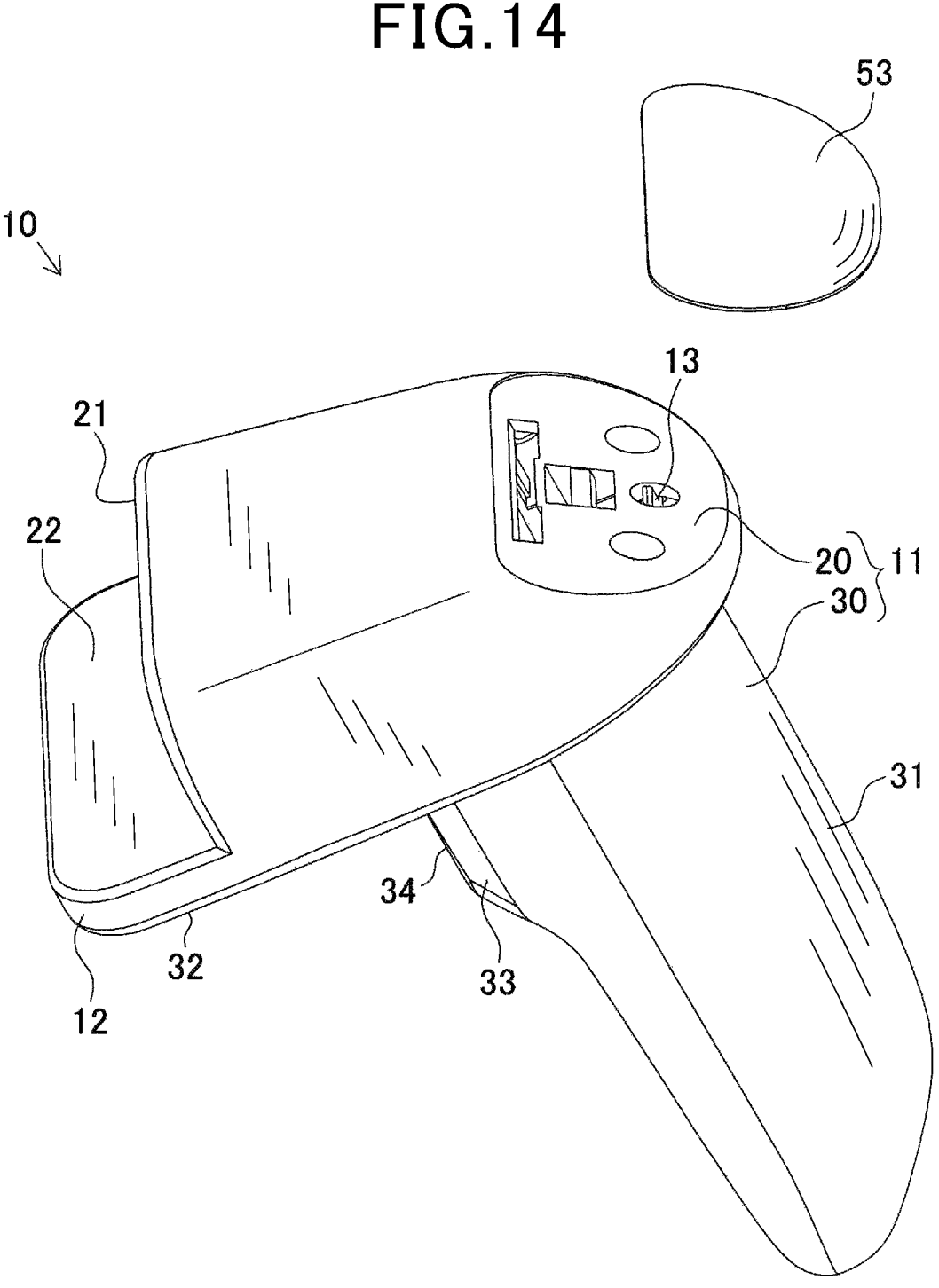
FIG. 14 is a perspective view showing a feature of an optical information reader according to a sixth embodiment.

As shown in FIG. 14, the upper case 20 of the housing 11 has a sound emission hole 13 for emitting the buzzer sound emitted by the buzzer 47, which is housed inside housing 11, to the outside. In order to keep the sound emission hole 13, the sound emission hole 13 is closed by a sheet material such as a PET sheet (hereinafter referred to simply as sheet 53) that is adhered to the upper case 20 using double-sided tape 54. In the present embodiment, the buzzer 47 corresponds to an example of a "sounding unit or notification unit" that is provided in housing 11 and is configured to emit a buzzer sound serving as a predetermined sound.

Figure 15:
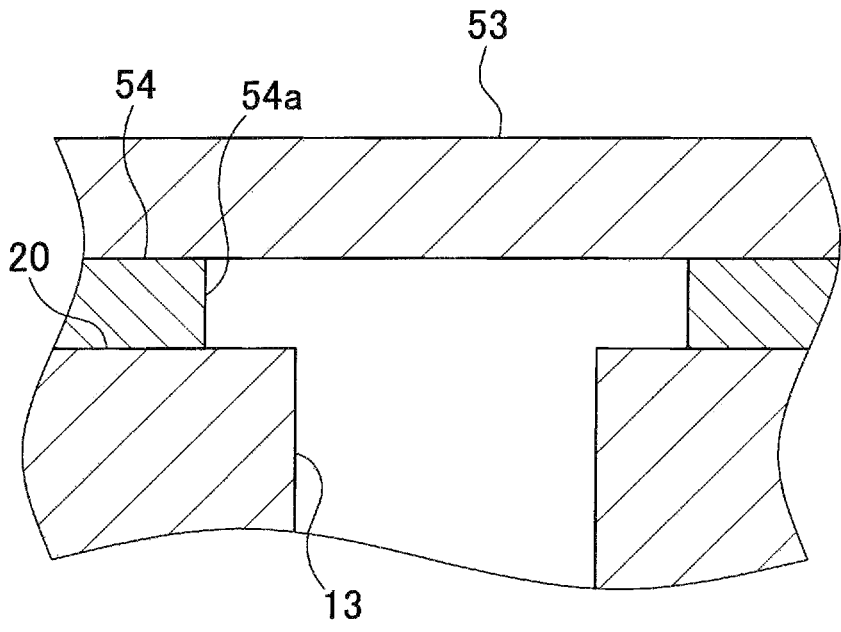
FIG. 15 is a partial sectional view outlining a structural relationship between the aperture of a double-sided tape that adheres a sheet and a sound emission hole.

In the embodiment, a reduction in the sound pressure of the buzzer sound emitted outside through the sound emission hole 13 is suppressed. Therefore, as shown in FIG. 15, an opening 54a larger than the sound emission hole is formed in the double-sided tape 54.

This means that even when double-sided tape 54 is used to adhere sheet 53 to housing 11 so that the sound emission hole 13 is closed, the double-sided tape 54 will not cover the sound emission hole 13. Therefore, compared to the case where even the double-sided tape covers the sound emission hole 13, the reduction in the sound pressure of the buzzer sound can be suppressed.

The characteristic configuration of this embodiment, in which the opening 54a larger than the sound emission hole 13 is formed in the double-sided tape 54 that adheres the sheet 53, can be applied to other embodiments and modifications thereof.

Seventh Embodiment

With reference to the accompanying drawings, an optical information reader according to a seventh embodiment of the present invention will now be described. This seventh embodiment differs from the first embodiment, described above, mainly in that the seventh embodiment provides predetermined notification to prevent forgetting to perform cleaning tasks such as wiping and disinfecting of the reader. Thus, the same symbols are attached to the components that are substantially the same as those in the first embodiment, and their descriptions are omitted.

Cleaning work such as wiping and disinfection of the optical information reader 10 needs to be performed periodically. Therefore, it is necessary to prevent forgetting to perform such work.

Figure 16:
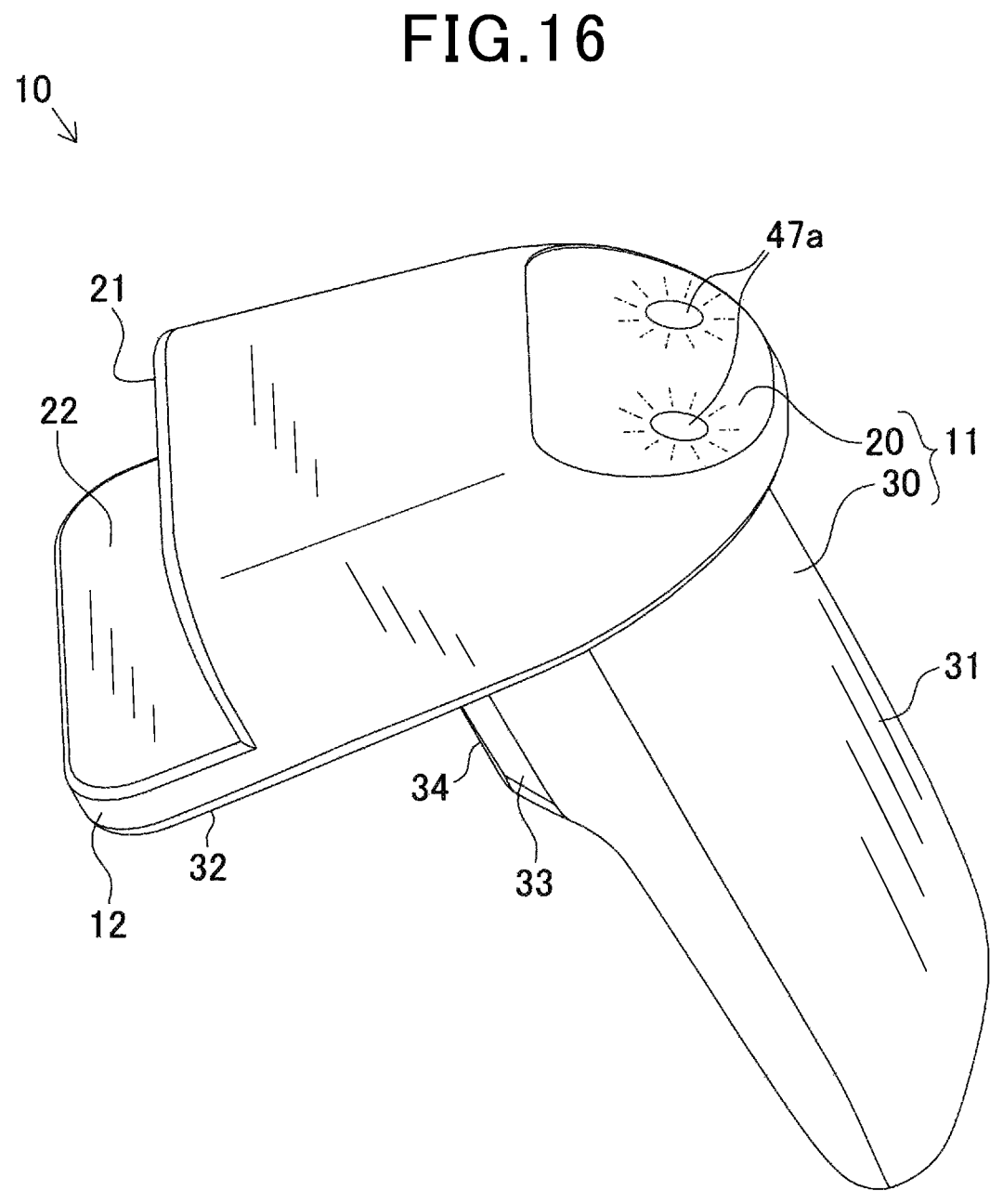

For this reason, as an example, in the present embodiment, information on the work schedule of the above cleaning work is stored in advance in the memory unit 42. In this example, at predetermined times according to that work schedule, cleaning instruction information that prompts cleaning work is reported. This cleaning instruction information can be aurally reported using buzzer sounds from the buzzer 47 or voice guidance through an abbreviated loudspeaker. Furthermore, the cleaning instruction information may be visually reported using the LED 47a provided on the upper case 20, for example, as illustrated in FIG. 16. The cleaning instruction information may be configured to be reported using vibration by the vibration actuator (vibrator) 51 described above, or light emission by LEDs or other devices belonging to illumination unit 44. The above cleaning instruction information may be reported at the time when the cleaning operation should start now, or may be reported at the time when the cleaning operation should start and after a predetermined time from now. The busser 47, LED 47a, and speakers can be examples of "reporting units" that report cleaning instruction information.

This notification of cleaning instruction information not only makes it easier to perform cleaning work at the right time for that cleaning work, but also prevents forgetting to perform the work.

In addition, the cleaning instruction information described above is not limited to being reported in response to information on the work schedule stored in advance in memory unit 42, but may also be reported in response to instructions received from the upper-level terminal 1 via the communication unit 46. This allows the upper-level terminal 1 to easily adjust the timing of reporting the above cleaning instruction information. When the reader is loaded on the loading stand 100, the above cleaning instruction information may be received from the upper-level terminal 1 via the loading stand 100, for example, or directly from the upper-level terminal 1 at a predetermined timing using wireless communication or other means.

The system, including the reader, can also be configured to acquire worker information that identifies the worker who performed the cleaning work, and this acquired worker information can be stored in the memory unit 42 together with information about the cleaning work. This allows not only easy management of work history, etc. based on the information stored in the memory unit 42, but also easy adjustment of the timing of reporting the above cleaning instruction information in order to match the actual work situations. The worker information can be obtained, for example, by reading the information code in which the worker information is encoded in the above reading process. In the configuration for this example, the controller 41 and imaging unit 43, which function as "reading devices," correspond to an example of an "acquiring unit" that acquires worker information.

As another example, a cleaning detector that can detect the status of cleaning work performed on the optical information reader 10 may be provided, and the detection results of this detector may be stored in the memory unit 42. As such a cleaning work detector, for example, a sensor (e.g., a sensor with a function equivalent to the piezoelectric sensor employed by the foregoing detector 45) can be employed at the location where the housing 11 is subjected to pressure by the operator who performs wiping during cleaning. Also, for example, using the fact that when the housing is wiped with alcohol, the temperature of its outer surface drops, a temperature sensor capable of detecting such a temperature drop may be employed as the above cleaning operation detector. An alcohol sensor may also be employed as the detector for the foregoing cleaning tasks. This allows a more reliable work history to be kept, and the timing of reporting the above cleaning instruction information can be adjusted to the actual situation.

It may also be configured so that at least part of the work history, etc. stored in the memory unit 42 as described above is transmitted to the upper-level terminal 1 via the communication unit 46. This can be configured such that the foregoing cleaning instruction information is reported in response to instructions received from this upper-level terminal 1 via the communication unit 46. This allows the upper-level terminal 1 to easily grasp the work history regarding the optical information reader 10 to be managed.

Thus, the timing of reporting the foregoing cleaning instruction information can be appropriately adjusted to the actual work situation.

The characteristic configuration of this embodiment and modifications, such as reporting cleaning instruction information to encourage cleaning work, can be applied to other embodiments and modifications thereof.

Eighth Embodiment

With reference to the accompanying drawings, an optical information reader according to an eighth embodiment of the present invention will now be described.

This eighth embodiment differs from the first embodiment, described above, mainly in that the eighth embodiment is configured to determine if the patient whose temperature is measured is in a febrile state. Thus, the same reference symbols are attached to the components that are substantially the same as those in the first embodiment, and their descriptions are omitted.

Figure 17:
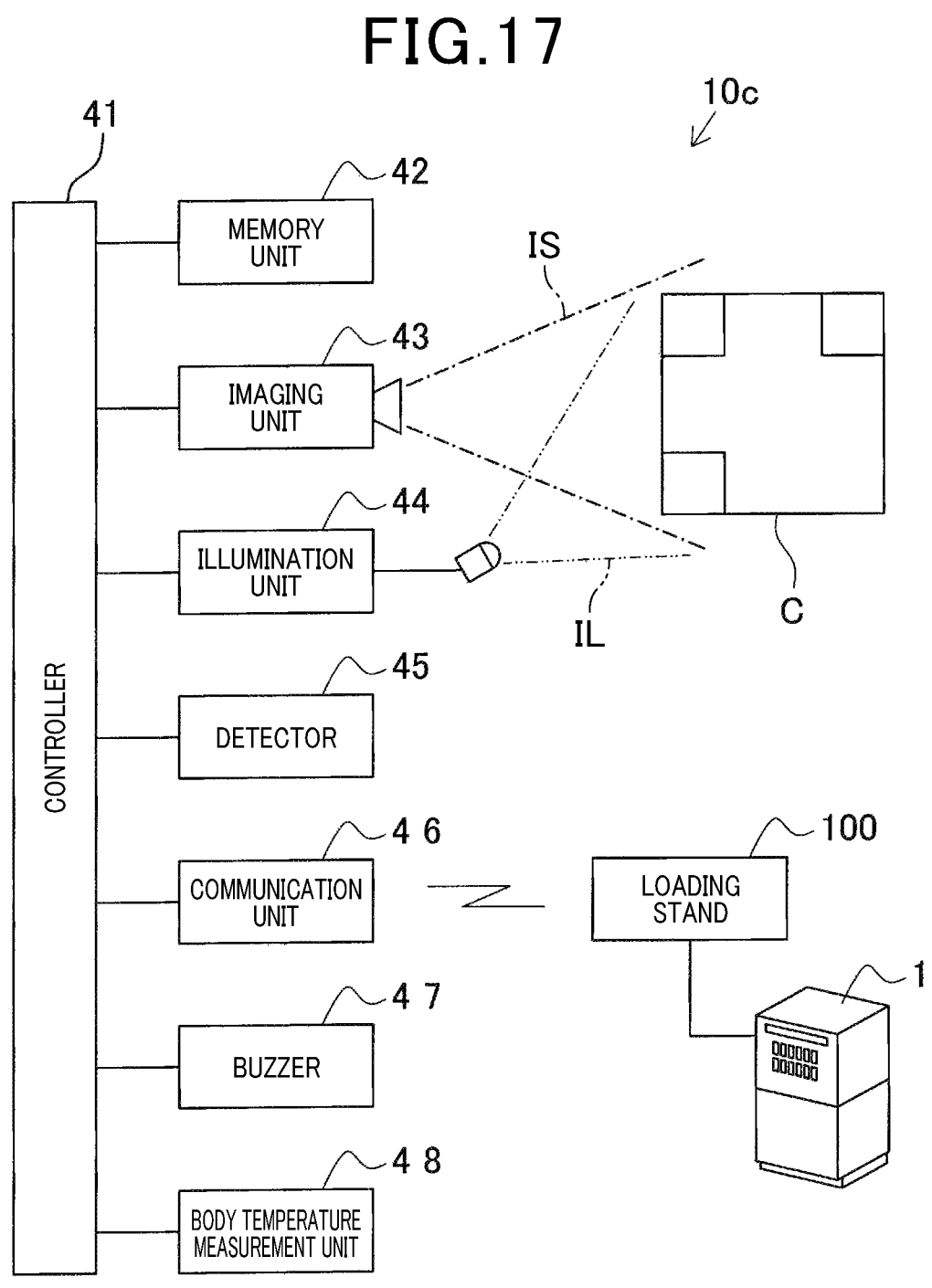
FIG. 17 is a block diagram exemplifying an outline of electric configurations and some other configurations of the optical information reader.

As shown in FIG. 17, an optical information reader 10c is equipped with a body temperature measuring device 48 that can measure the patient's body temperature. The body temperature measuring device 48 is provided as an infrared emitting thermometer, positioned within the housing 11 and configured to measure the body temperature at a site of the patient to which the reading port 21 is directed.

Figure 18:
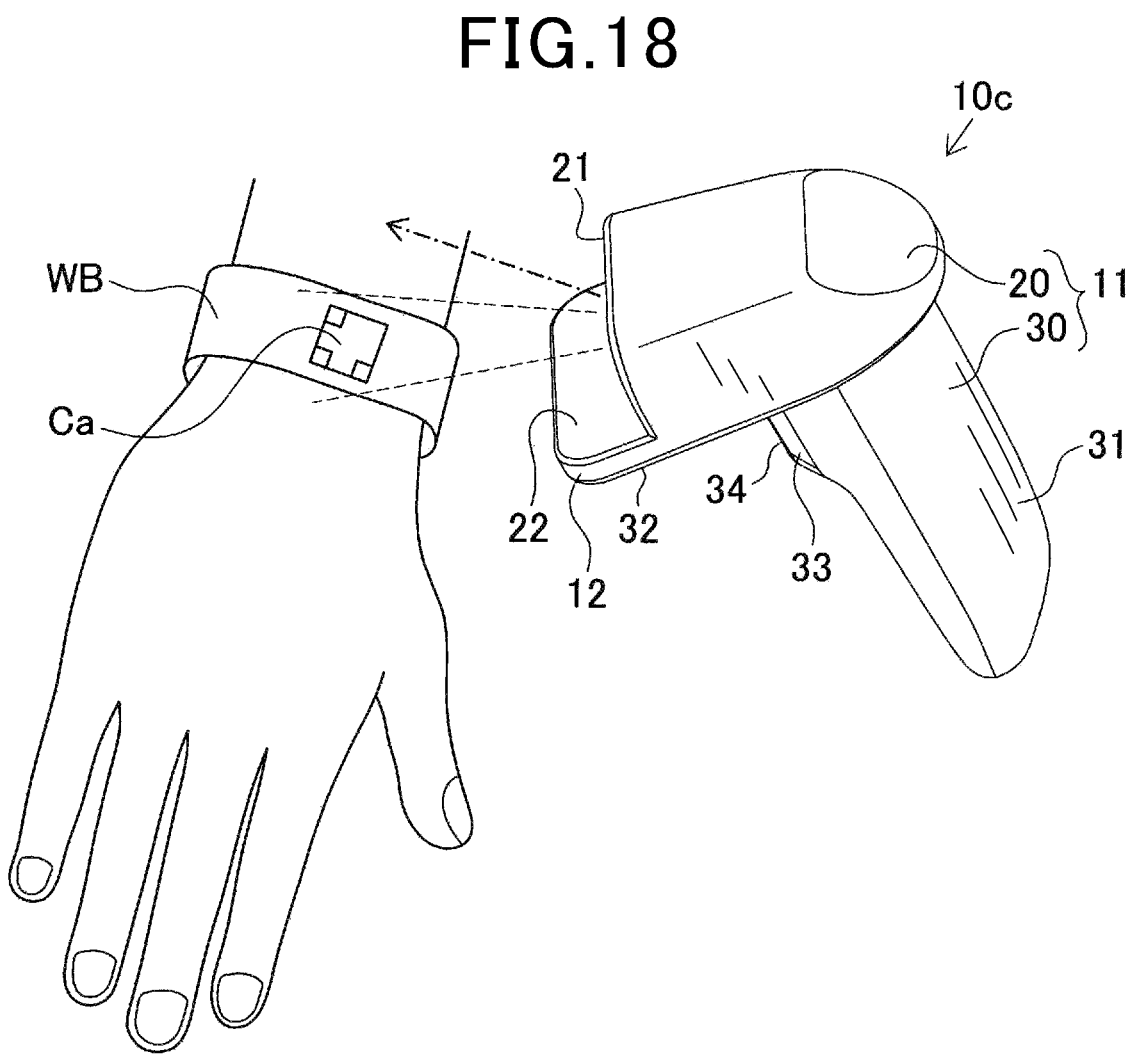
FIG. 18 is an illustration showing how the reading port of the optical information reader is directed to a patient's wristband.

In the present embodiment, patient information identifying a patient and average body temperature information of the patient are stored in the memory unit 42 in a database form to be associated to each other. In addition, the information code Ca, which is an encoded code of the above patient information, is displayed on the patient's wristband WB. Therefore, as illustrated in FIG. 18, the foregoing reading process is started with the reading port 21 oriented to the patient's wristband WB. This allows the body temperature near the patient's wrist to be measured by the body temperature measuring device 48 when the patient information is read from the above information code Ca.

Then, a fever determination process is performed by the controller 41. Through this process, the average body temperature information associated with the patient information read from the above information code Ca is compared with measurement results of the body temperature measuring device 48. This allows a determination to be made as to whether the patient is in a febrile state or not. In this example, a single pressing operation on the operating surface portion 34 may be used to read the information code Ca and measure the body temperature by the body temperature measuring device 48. After the patient information is read from the imaged information code Ca by the first pressing operation, the second pressing operation may be used to measure the body temperature by the body temperature measuring device 48. The controller 41 that performs the above fever determination process functionally corresponds to an example of a "determination unit" that determines whether the patient is in a fever state.

Thus, not only can a patient's body temperature be measured using the optical information reader 10c that can be easily disinfected by wiping, but also whether the patient has a fever can be easily ascertained. This reduces the nursing burden on the patients.

The patient information and the average body temperature of the patient may be stored in a database, for example, at upper-level terminal 1. In this case, the read patient information and the measurement results of the body temperature measuring device 48 can be sent to the upper-level terminal 1. Therefore, the upper-level terminal 1 can determine whether the patient has a fever or not, and the reader can receive the result of this determination from the upper-level terminal 1.

Patient information may also include medical record information that should be used to make medication decisions, etc. for that patient. In such a case, the medical record information and the measurement results of the body temperature measuring device 48 may be used to inform information that assists in medication decisions, etc.

The characteristic configuration of this embodiment of determining whether a patient whose body temperature is measured is in a febrile state can be applied to other embodiments and their modifications.

Ninth Embodiment

With reference to the accompanying drawings, an optical information reader according to a ninth embodiment of the present invention will now be described.

This ninth embodiment differs from the first embodiment, described above, mainly in that the eighth embodiment is provided with a coil for wireless power transmission which is bonded to an inner surface on a reading port side in a laminate-shaped extension. Thus, the same reference symbols are attached to the components that are substantially the same as those in the first embodiment, and their descriptions are omitted.

Figure 19:
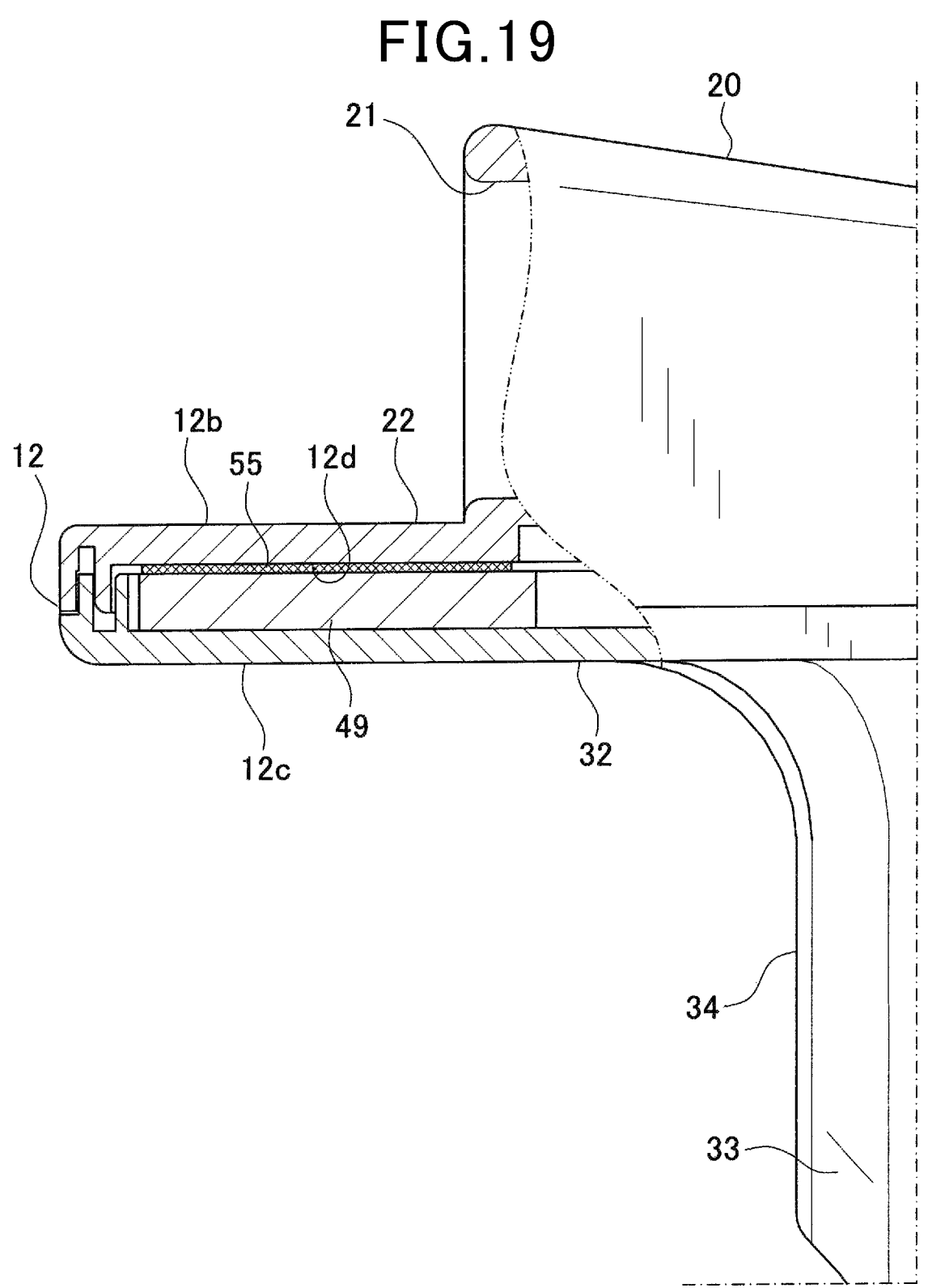
FIG. 19 is a partially enlarged sectional view showing a feature of an optical information reader according to a ninth embodiment.

As shown in FIG. 19, an extension 12 is provided in the form of a laminate-shaped plate extending forward from between the lower edge of the gripping handle side of the reading port 21 and the gripping handle 31 in the direction along which the reading port 21 is directed. Inside the extension 12, a coil member for wireless power transmission (hereinafter referred to simply as coil 49) is located.

Thus, the coil 49 is positioned within the extension 12, which extends in a laminate-shaped plate. Therefore, heat generated in the coil 49 during power transmission can be dissipated from the reading port side (hereinafter referred to as "reading port side surface 12b") and the gripping handle side (hereinafter referred to as "loading side surface 12c") of the extension 12, respectively. The longer the length of the extension, the larger the heat dissipation area by the reading port side surface 12b and the loading side surface 12c. Therefore, depending on the length of the extension 12, heat dissipation performance with respect to the heat generated by the coil 49 can be improved. In addition, the heat generated in the coil 49 can be difficult to transfer to the various electronic components housed inside the housing 11 that is different, as components, from the extension 12.

In particular, in this embodiment, the coil 49 is bonded to the inner surface 12d, which is the reading port side, of the inner surface of the housing portion comprising the inner surface of extension 12, using a thermally conductive adhesive 55, but not bonded to the inner surface thereof positioned on the ripping handle side. The power supply is received by placing the loading side surface 12c of the extension 12 on the charging surface of the loading stand 100, which acts as a charger. In this case, the heat dissipation of the loading side surface 12c is poor due to the proximity to the charging surface. However, the heat dissipation of the reading port side surface 12b of extension 12 is not affected by the charging surface. Therefore, by bonding the coil 49 to the inner surface 12d located on the reading port side, the heat generated in the coil 49 during charging is more easily transferred to the reading port side surface 12b, which has higher heat dissipation performance. This further improves the heat dissipation effect of the laminate-shaped extension 12.

The characteristic configuration of this embodiment, in which the coil 49 for wireless power transmission is located in the extension 12 extending in the form of a thin plate, can be applied to other embodiments and modifications thereof.

Tenth Embodiment

With reference to the accompanying drawings, an optical information reader according to a tenth embodiment of the present invention will now be described.

This tenth embodiment differs from the first embodiment, described above, mainly in that the configuration according to the tenth embodiment is provided with a protrusion protruding from a central area of the operating surface portion inside the gripping handle. Thus, the same reference symbols are attached to the components that are substantially the same as those in the first embodiment, and their descriptions are omitted.

Figure 20:
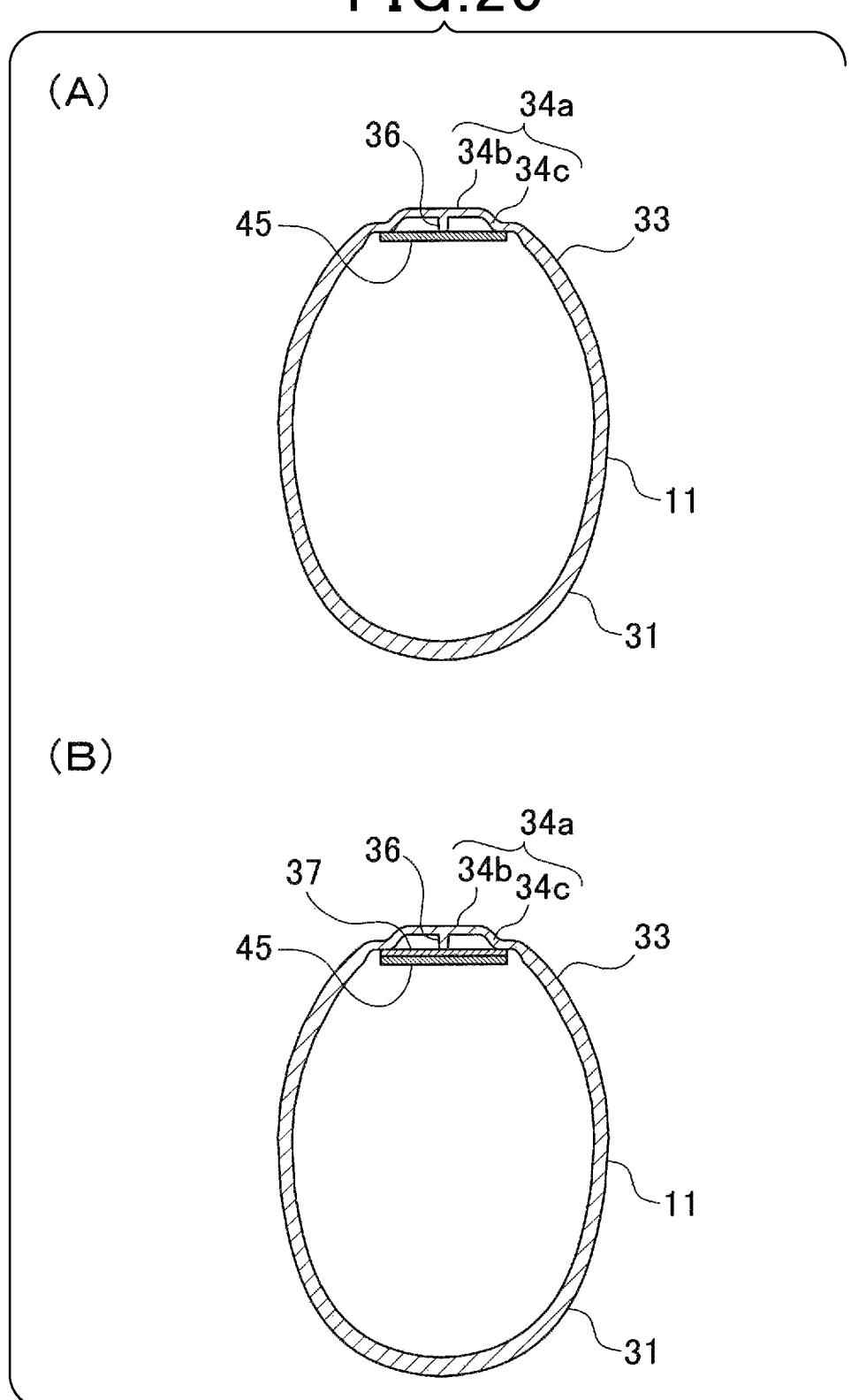
FIG. 20, part (A) thereof, is an explanatory diagram along a section taken along the X-X line in FIG. 3, outlining a feature of an optical information reader according to a tenth embodiment, and FIG. 20, part (B), is an explanatory diagram along the section taken along the X-X line in FIG. 3, outlining a feature of an optical information reader according to a modification of the tenth embodiment.

As shown in part (A) of FIG. 20, the gripping handle 31 of the housing 11 is provided with a protrusion 36 protruding inwardly at a position on the inner surface side of the central surface portion 34*b* included in the operating surface portion 34*a*. In addition to this protrusion, the detector 45 is configured to detect the distortion caused in the operating surface portion 34*a* according to the inward deformation of the protrusion 36.

When the operating surface portion 34*a* is touched by the operator or user, the central surface portion 34*b* is the most deformed. Therefore, the protrusion 36 located on the inner surface side of this central surface portion 34*b* can exhibit larger inward movement. Thus, the detection accuracy of the detector 45, i.e., the operability of the reader and system can be improved compared with the configuration with no protrusion.

The peripheral surface portion 34*c* functions as the fulcrum of deformation when the operating surface portion 34*a* is touched by an operator. The peripheral surface portion 34*c* is thinner than the central surface portion 34*b* because of the presence of protrusion 36. This makes the operating surface portion 34*a* even more easily deformable, which further improves the detection accuracy of the detector 45. On the other hand, the thickness of the central surface portion 34*b* of housing 11 will increase. Therefore, compared to the case where the entire operating surface portion 34*a* is thin-walled due to the absence of protrusions 36, resin flow during resin molding in the vicinity of the operating surface portion 34*a* is improved during manufacturing, and molding defects can thus be suppressed or reduced.

As a modification of this embodiment, an elastic member 37 such as a rubber member may be interposed between the protrusion 36 and the detector 45, as illustrated in part (B) of FIG. 20. This allows the stress transmitted to the detector 45 to be adjusted according to factors which include the thickness and elasticity of the elastic member 37. For example, an excessive pressing force can be absorbed by the elastic member 37 to prevent damage to the detector 45.

The characteristic configuration of the present embodiment in which the protrusion 36 is provided on the central inner surface side of the operating surface portion can be applied to other embodiments and modifications. For example, it can be applied to an operating surface portion 34 where the central surface portion does not protrude outward as described. The characteristic configuration in which the elastic member 37 is interposed between the protrusion 36 and the detector can also be applied to other embodiments and modifications.

Eleventh Embodiment

With reference to the accompanying drawings, an optical information reader according to an eleventh embodiment of the present invention will now be described.

The eleventh embodiment differs from the third embodiment, described above, mainly in that a pair of magnets lined up with different polarities in the insertion/extraction directions are used for mounting and fixing. Thus, the same reference symbols are attached to the components that are substantially the same as those in the third embodiment, and their descriptions are omitted.

In the case of the configuration for loading the optical information reader 10*b* on the loading stand 100*a* at a predetermined position (the most suitable position for charging, etc.) using the attraction between the magnet 52 of the optical information reader 10*b* and the magnet 102 of the loading stand 100*a* as explained in the third embodiment above, it is necessary to adjust the attraction force appropriately. If the attractive force between the magnets 52 and 102 is too strong, the force required to pick up the optical information reader 10*b* from the loading stand 100*a* will increase. On the other hand, if the above attractive force is weakened too much, the holding power using magnets will be weakened.

In particular, an attractive force generated in the direction perpendicular to a direction in which the two magnets face each other (in the example in FIG. 10, the vertical direction) is about 20-30% weaker than an attractive force generated in the direction perpendicular to that facing direction (in the example in FIG. 10, the horizontal direction). This allows the above attractive force to be weakened to the extent that the reader is easy to remove. However, in that case, when an external force is applied in a direction perpendicular to the above-mentioned facing direction (in this embodiment, along the mounting surface 101), the optical information reader 10*b* may shift from the above-mentioned predetermined position or may detach from the loading stand 100*a*. That is, there is a possibility that this may happen.

Figure 21:
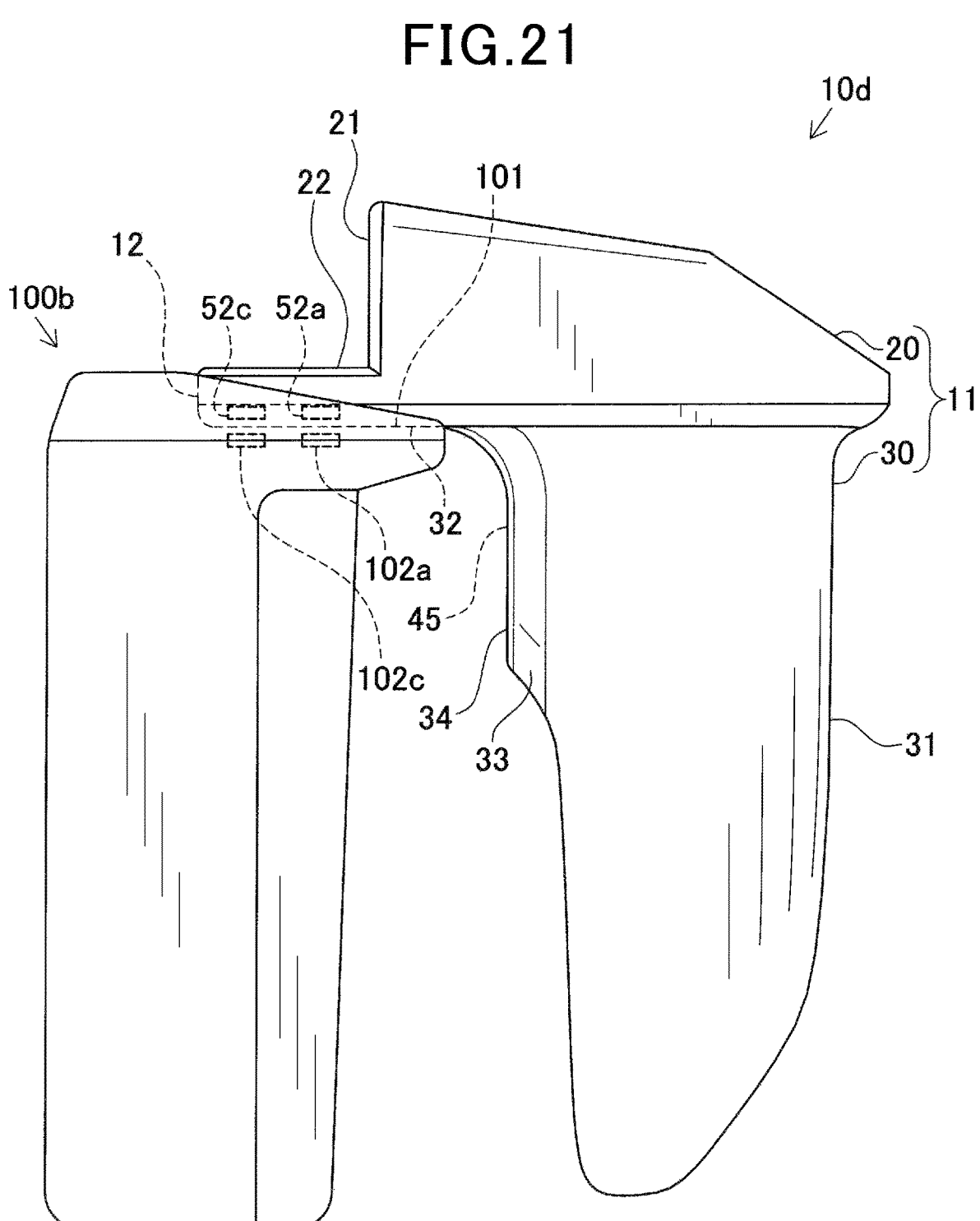
FIG. 21 is a side view showing both an optical information reader and a loading stand which are according to an eleventh embodiment.
Figure 22:
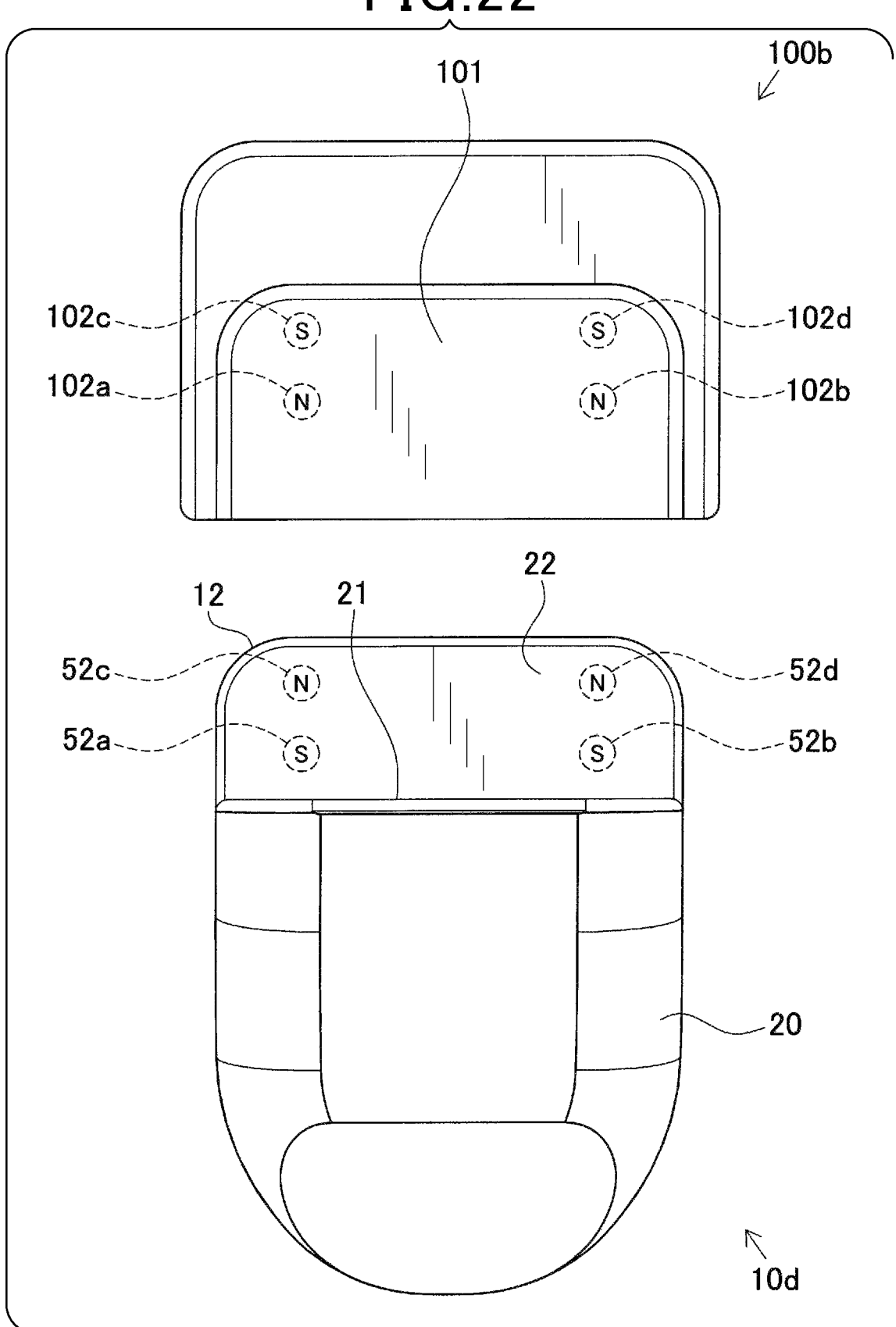
FIG. 22 is an illustration explaining how a magnet provided to the optical information reader and a magnet provided to the loading stand are arranged positionally in the configurations shown in FIG. 21.

Therefore, in this embodiment according to the optical information reader 10*d* and loading stand 100*b*, a pair of magnets lined up with different polarity in the predetermined direction along the loading surface 101 (hereinafter also referred to as insertion/extraction directions) are arranged, as illustrated in FIGS. 21 and 22. This allows the optical information reader 10*d* to be held in the above predetermined position relative to the loading stand 100*b*.

Figure 24:
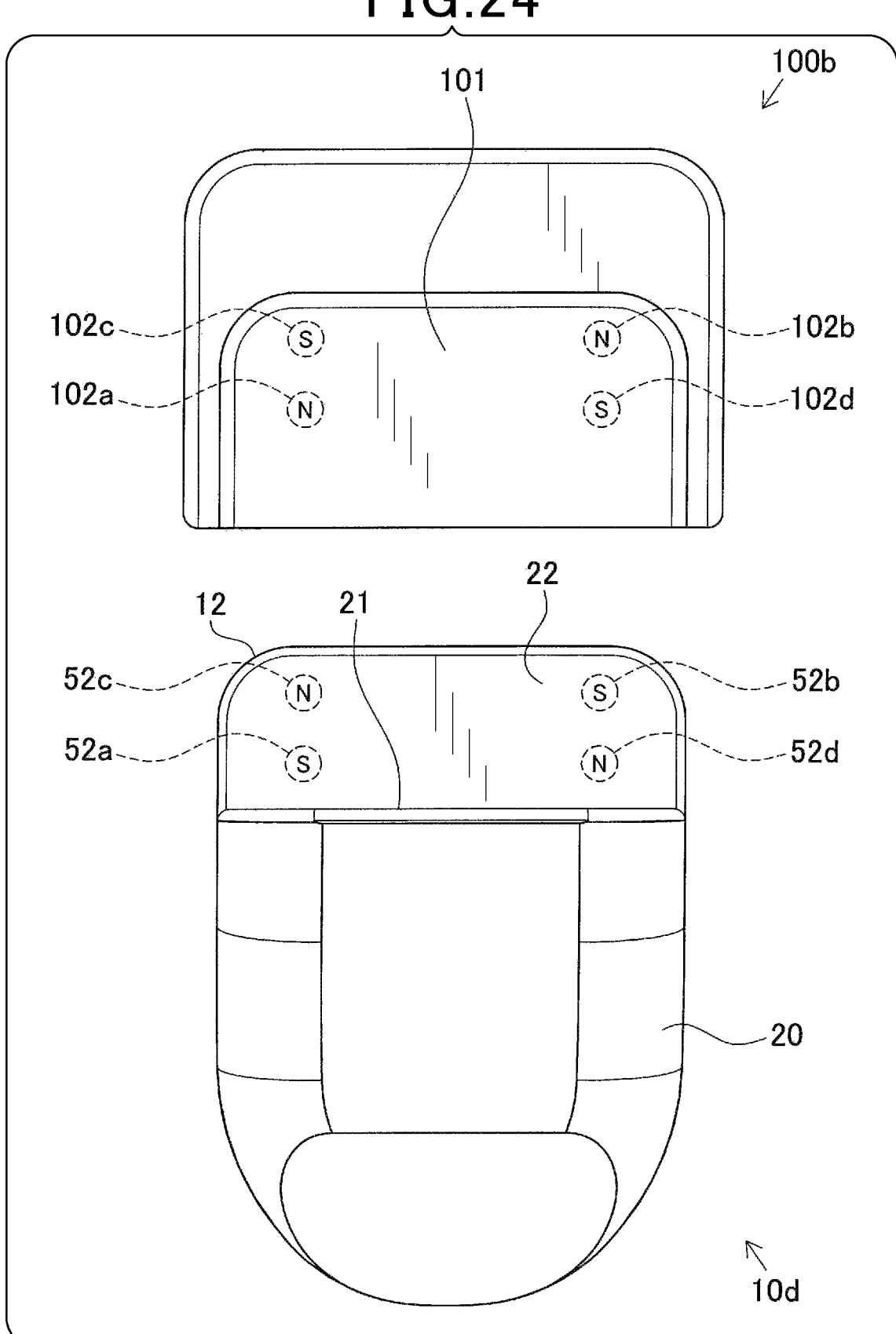
FIG. 24 is an illustration explaining how a magnet provided to the optical information reader and a magnet provided to the loading stand are arranged positionally in a modification of the eleventh embodiment.

Specifically, in the optical information reader 10*d*, the extension 12 has a rectangular area on its lower inner surface side that is opposite the loading surface 101. Four magnets of the same size, 52*a*-52*d*, are provided at the four corners of this rectangular area. The magnets 52*a* and 52*b* located on the gripping handle side are arranged so that their poles directed to the loading surface 101 are S-poles, and the magnets 52*c* and 52*d* located on the side facing the gripping handle are arranged so that their poles directed to the loading surface 101 are N-poles. The magnets 52*a* and 52*c* consist of a pair of magnets that are positioned at a predetermined distance in the insertion/extraction directions (e.g., about one times the length of magnet 52*a* along the insertion/extraction directions) and are aligned in such a way that their polarities are different. Similarly, the magnet 52*b* and magnet 52*d* are a pair of magnets with the positional relationship that the magnets 52b and 42d are separated by the above predetermined interval in the insertion/extraction directions and lined up in different polarities. The above predetermined interval can be changed according to factors including the magnetic force and shape of each magnet 52a (to 52d). For example, the interval may be set at a distance of 0.5 to 2 times the length of the magnet 52a in the insertion/extraction directions. In FIG. 22, and FIG. 24 which will be described below, for convenience of explanation, the magnetic poles directed to the loading surface 101 are "S" poles for magnets 52a and 52b, while the magnetic poles directed to the loading surface 101 are "N" poles for magnets 52c and 52d.

The loading stand 100b has the loading surface 101 facing the optical information reader 10d, which is loaded in the foregoing position of the stand. On the inner side of this loading surface, a magnet 102a, which is directed toward the magnet 52a and has an N-pole, is loaded in a position which is opposed to the magnet 52a. A magnet 102b, which is directed toward the magnet 52b and has an N-pole, is loaded in a position which is opposed to the magnet 52b. Moreover, a magnet 102c, which is directed toward the magnet 52c and has an S-pole, is loaded in a position which is opposed to the magnet 52c. Moreover, a magnet 102d, which is directed toward the magnet 52d and has an S-pole, is loaded in a position which is opposed to the magnet 52d.

Figure 23:
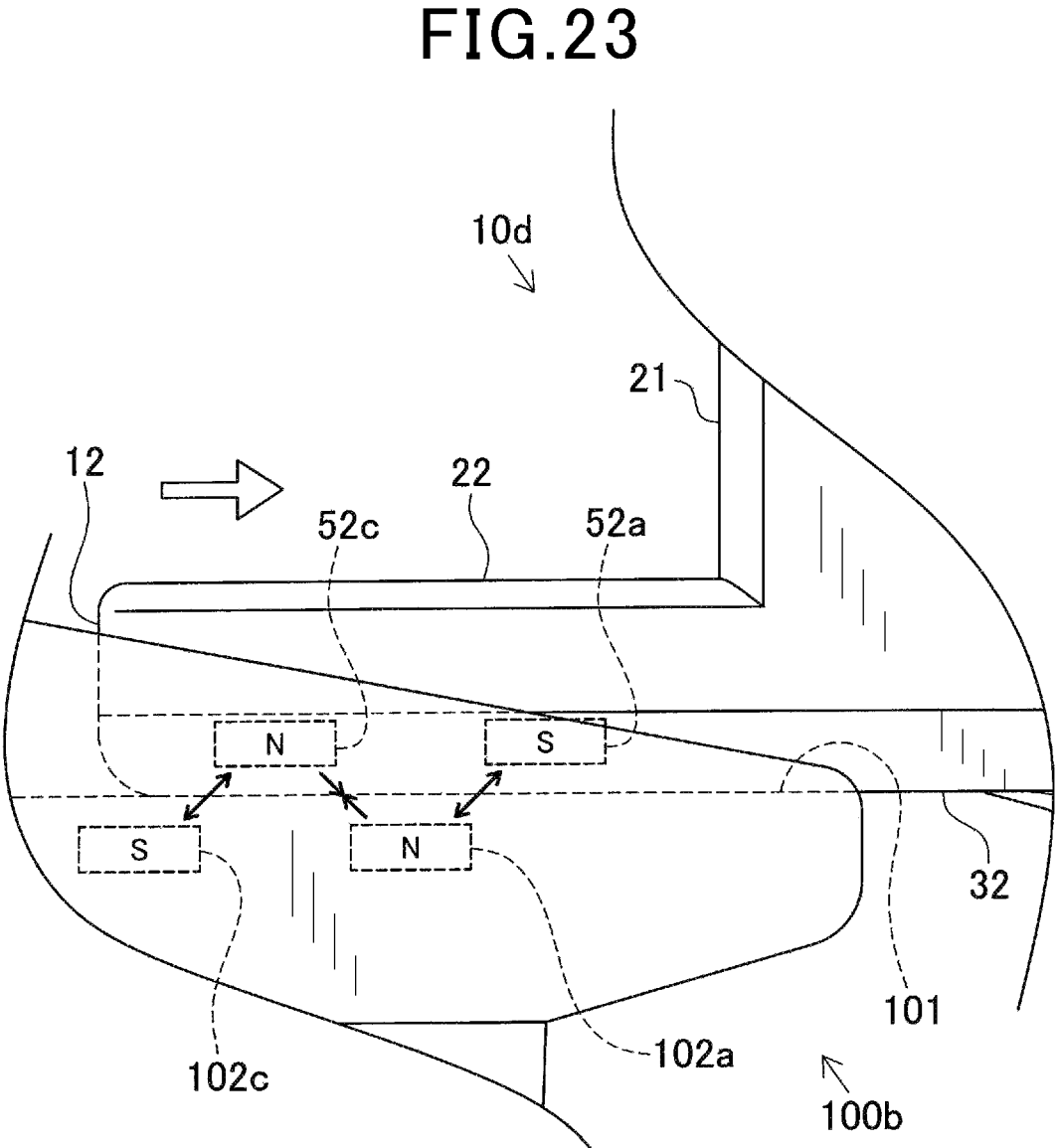
FIG. 23 is an illustration explaining attractive and repulsive forces generated between the magnet of the optical information reader and the magnet of the loading stand.

This ensures that even if an external force (external force to the right in FIG. 23) acts on the optical information reader 10d to pull it out along the foregoing insertion/extraction directions, a counterforce against the external force can be secured. In other words, as illustrated in FIG. 23, in addition to an attractive force generated between the magnets 52a and 102a and an attractive force generated between the magnets 52c and 102c, a repulsive force generated between the magnets 52c and 102a acts to counter the external force. At the same time, in addition to an attractive force between generated the magnets 52b and 102b and an attractive force generated between the magnets 52d and 102d, a repulsive force generated between the magnets 52d and 102b act to oppose the external force.

In FIG. 23, for convenience of explanation, the magnetic pole of the magnet 52a which is near the loading surface 101 is magnetized to the "S" pole. Furthermore, the magnetic pole of the magnet 52c which is near the loading surface 101 is magnetized to the "N" pole. The pole of magnet 102a which is near the magnet 52a is magnetized to the "N" pole, while the pole of magnet 102c which is near the magnet 52c is magnetized to the "S" pole.

In addition, even if an external force (leftward external force in FIG. 23) acts on the optical information reader 10d to push it along the foregoing insertion/extraction directions, it can still be opposed to the external force. In other words, in addition to an attractive force generated between the magnets 52a and 102a and an attractive force generated between the magnets 52c and 102c, a repulsive force generated between the magnets 52a and 102c acts to oppose such an external force. At the same time, in addition to an attractive force generated between the magnets 52b and 102b and an attractive force generated between the magnets 52d and 102d, a repulsive force generated between the magnets 52b and 102d acts to oppose such an applied external force.

Thus, the respective pairs of magnets lined up with different polarities in the insertion/extraction directions, respectively, are used for attractive required between the optical information reader 10d and the loading stand 100b. This allows the foregoing attractive and repulsive forces generated as described above, to be used as holding forces against the external force. Therefore, a strong holding structure that can resist external forces in the insertion/extraction directions can be obtained without excessively increasing the attraction forces with the magnets.

A modification of this embodiment is illustrated in FIG. 24. In the magnet arrangement shown in FIG. 22, the magnets 52b and 52d may be interchanged mutually and the magnets 102b and 102d may be interchanged mutually. Even in this magnet arrangement, each pair of magnets lined up with different polarities in the insertion/extraction directions can be used for the removable connection required between the optical information reader 10d and the loading stand 100b, thus still providing the foregoing advantageous effects.

The characteristic configuration of the present embodiment and its modifications, in which each pair of magnets arranged in different polarities in the insertion/extraction directions are used for loading and fixation, can be applied to other embodiments and modifications in the same way as described.

The invention is not limited to the above embodiments, etc., but may be embodied, for example, as follows.

(1) The housing 11 is not limited to being composed of two cases, upper case 20 and lower case 30, but may be composed of three or more cases. Even in this configuration, the above effect is achieved when the gripping handle 31 and operating surface portion 34 are formed at a site where the cases are not connected to each other and where the site is formed on one of the plurality of cases. The gripping handle 31, etc. are not limited to being formed by a single case, but may be formed, for example, by utilizing multiple cases that are assembled so that the effect of grooves, steps, etc. is reduced.

(2) The controller 41 is not limited to starting the reading process when the detector 45 detects that the operator has touched the operating surface portion 34, assuming that the above operation to start reading has been detected. Instead of this, the controller 41 may also start other predetermined processes related to the reading device, such as switching reading modes.

(3) The present invention is not limited to the application to an optical information reader 10 that wirelessly transmits the reading results, etc. obtained in the reading process to an upper-level terminal, etc. via communication unit 46. Alternatively, the invention may be applied to an optical information reader that transmits reading results, etc. to an upper-level terminal, etc. via a cable drawn from a part of the lower case 30 different from the gripping handle 31, for example, the lower end of the lower case 30.

(4) The invention is not limited to application to an optical information reader 10 that optically reads information codes, but may also be applied to an optical information reader that optically reads optical information, including character information, by imaging the optical information.

DESCRIPTION OF PARTIAL NUMBERS

1 . . . upper-level terminal
10a to 10d . . . optical information reader
11 . . . housing
12 . . . extension
13 . . . sound emission hole
20 . . . upper case
21 . . . reading port
30a . . . lower case
31 . . . gripping handle
34, 34a . . . operating surface portion 34*b* . . . central surface portion
34*c* . . . peripheral surface portion
36 . . . protrusion
41 . . . controller (reading device, acquiring unit, determination unit)
42 . . . memory unit
43 . . . imaging unit (reading device, acquiring unit)
45 . . . detector
47 . . . buzzer (sound generating unit, reporting unit)
47*a* . . . LED (reporting unit)
48 . . . body temperature measuring device
49 . . . coil (coil for wireless power transmission)
51 . . . vibration actuator (vibrator)
52 . . . magnet
53 . . . sheet
54 . . . double-sided tape
54*a* . . . opening
100, 100*a*, 100*b* . . . loading stand
C . . . information code (optical information)
G . . . center of gravity

What is claimed is:

1. An optical information reader comprising:
a reading device which optically reads optical information and includes a piezoelectric sensor; and
a housing having a plurality of cases and formed by mutually combining the plurality of cases such that the housing forms a housing space therein in which the reading device is housed,
wherein
one case of the plurality of cases forms a gripping handle which is manually grippable by an operator when the operator makes the reading device execute predetermined processing for reading the optical information,
the gripping handle includes a predetermined operating surface portion, an outside surface of the predetermined operating surface portion being touchable by the operator when the operator grips the gripping handle,
the piezoelectric sensor of the reading device (i) is inside the gripping handle at a site on the predetermined operating surface portion and (ii) is configured to sense distortion caused on the predetermined operating surface portion,
a thickness of the predetermined operating surface portion is thinner than other portions of the gripping handle such that a pressing operation by the operator on the outside surface of the predetermined operating surface portion causes the distortion, and
a part of the housing at which the gripping handle is formed has no joint provided between cases of the plurality of cases.

2. The optical information reader of claim 1, wherein the predetermined operating surface portion is formed as an operating base having a flat surface protruding outward from the gripping handle, the operating base being thinner than the other portions of the gripping handle.

3. The optical information reader of claim 1, further comprising a vibrator which vibrates when the predetermined operating surface portion is touched by the operator, the vibrator being arranged at another position in the gripping handle that is opposed to the predetermined operating surface portion.

4. A system comprising:
the optical information reader of claim 1; and
a loading stand, having a loading surface on which the optical information reader is loaded, wherein a magnet is arranged at a position located inside the housing of the optical information reader, the position being opposed to a further part of the housing.

5. The system of claim 4, wherein the gripping handle is not formed at the further part of the housing.

6. The optical information reader of claim 1, wherein
the predetermined operating surface portion has a central surface portion and a peripheral surface portion around the central surface portion, the central surface portion being protruded further outward than the peripheral surface portion, and
the piezoelectric sensor is configured to detect distortion caused in the peripheral surface portion.

7. The optical information reader of claim 6, wherein
the housing has a protrusion that protrudes inwardly and is positioned on and inside the central surface portion of the predetermined operation surface portion, and
the piezoelectric sensor is configured to detect distortion caused in the predetermined operating surface portion depending on amounts of inward changes of the protrusion.

8. The optical information reader of claim 1, wherein
the reading device is configured to optically read the optical information via a reading port formed on the housing,
the housing includes an extension that extends toward the reading port from a space between (i) a lower edge of the reading port that faces the gripping handle and (ii) the gripping handle, and
the optical information reader has a center of gravity such that, when the reader is projected to a predetermined surface on which the reader is loaded with both an upper edge of the reading port and a tip edge of the extension being directed downward, the center of gravity is contained in a range formed between (i) a contact portion provided between the upper edge and the predetermined surface and (ii) a contact portion provided between the tip edge and the predetermined surface.

9. The optical information reader of claim 1, wherein
the housing includes a sound generating unit that generates a predetermined sound,
the housing has a sound emission hole for sound emission of the predetermined sound to the outside, and
double-sided tape for bonding a sheet for closing the sound emission hole to the housing has an opening larger than the sound emission hole.

10. The optical information reader of claim 1, wherein
the optical information reader comprises a reporting unit that reports cleaning instruction information that prompts cleaning work of the optical information reader at predetermined timing.

11. The optical information reader of claim 10, wherein the reporting unit receives instructions from an upper-level terminal and reports the cleaning instruction information.

12. The optical information reader of claim 7, wherein the optical information reader comprises
an acquiring unit for acquiring worker information that identifies a worker who has performed the cleaning work, and
a memory unit in which the worker information acquired by the acquiring unit is stored together with information on the cleaning work.

13. The optical information reader of claim 12, wherein the optical information reader comprises a cleaning work detector capable of detecting a state in which cleaning work has been performed on the optical information reader, and the memory unit stores, therein, detection results detected by the cleaning work detector.

14. The optical information reader of claim 12, wherein at least part of the information stored in the memory unit is transmitted to an upper-level terminal, and the reporting unit receives instructions from the upper-level terminal and reports the cleaning instruction information.

15. The optical information reader of claim 1, further comprising:

a body temperature measuring device capable of measuring a body temperature of a patient when patient information identifying the patient is read from the optical information by the reading device; and a determination unit for determining whether or not the patient is in a febrile state based on the results of the measurement by the body temperature measuring device.

16. The optical information reader of claim 1, wherein the reading device optically reads the optical information through a reading port formed in the housing, the housing includes an extension that extends in a laminate shape in a direction toward the reading port from between a gripping handle side edge of the reading port and the gripping handle, and a coil for wireless power transmission is disposed within the extension.

17. The optical information reader of claim 16, wherein the coil for wireless power transmission is bonded to an inner surface of the housing portion comprising the extension, the inner surface to which the coil is bonded being located closer to the reading port than is a remainder of the inner surface.

18. The optical information reader of claim 1, wherein the plurality of cases comprises upper and lower cases, the lower case is configured to serve as the gripping handle, and the piezoelectric sensor is provided in the lower case at a site that is opposed to the predetermined operating surface portion.

* * * * *